US008969063B2

(12) United States Patent
Conner et al.

(10) Patent No.: US 8,969,063 B2
(45) Date of Patent: *Mar. 3, 2015

(54) HERPES SIMPLEX VIRUSES AND METHODS OF VIRAL REPLICATION

(75) Inventors: Joe Conner, Glasgow (GB); Susanne Moira Brown, Glasgow (GB)

(73) Assignee: Virttu Biologics Limited, Glasgow (GB)

(*) Notice: Subject to any disclaimer, the term of this patent is extended or adjusted under 35 U.S.C. 154(b) by 366 days.

This patent is subject to a terminal disclaimer.

(21) Appl. No.: 13/417,708

(22) Filed: Mar. 12, 2012

(65) Prior Publication Data

US 2012/0237999 A1 Sep. 20, 2012

Related U.S. Application Data

(63) Continuation of application No. 12/527,380, filed as application No. PCT/GB2008/000527 on Feb. 15, 2008, now Pat. No. 8,163,292.

(60) Provisional application No. 60/916,862, filed on May 9, 2007.

(30) Foreign Application Priority Data

Feb. 16, 2007 (GB) .................................. 0703066.1

(51) Int. Cl.
*C12N 7/00* (2006.01)
*C12N 5/10* (2006.01)
*C07K 14/47* (2006.01)
*C12N 15/86* (2006.01)
*A61K 48/00* (2006.01)

(52) U.S. Cl.
CPC ............ *C07K 14/4703* (2013.01); *C12N 15/86* (2013.01); *A61K 35/13* (2013.01); *A61K 48/00* (2013.01); *C12N 2710/16643* (2013.01)
USPC ....................................... 435/235.1; 435/325

(58) Field of Classification Search
CPC ........... C12N 2710/16651; C12N 2710/16051; C07K 14/4703
See application file for complete search history.

(56) References Cited

U.S. PATENT DOCUMENTS 8,163,292 B2 * 4/2012 Conner et al. ............. 424/199.1

FOREIGN PATENT DOCUMENTS

| CN | 1714871 A | 1/2006 |
| CN | 101058809 A | 10/2007 |
| WO | 00/23589 A2 | 4/2000 |
| WO | 2005/049845 A2 | 6/2005 |

OTHER PUBLICATIONS

Kim et al (PNAS 101: 16251-16256, 2004).*
Zhang et al (PNAS 104:9517-9522, 2007).*
Coukos, George et al., "Oncolytic Herpes Simplex Virus-1 Lacking ICP34.5 Induces p53-independent Death and Is Efficacious against Chemotherapy-resistant Ovarian Cancer," clinical Cancer Research, 2000, vol. 6, pp. 3342-3353.
Doyon, Yannick et al., "ING Tumor Suppressor Proteins Are Critical Regulators of Chromatin Acetylation Required for Genome Expression and Perpetuation," Molecular Cell, 2006, vol. 21, pp. 51-64.
Garkavtsev, Igor et al., "The candidate tumour suppressor protein ING4 regulates brain tumour growth and angiogenesis," Nature, 2004, vol. 428, pp. 328-332.
Gong Wei et al, "Function of the ING family of PHD proteins in cancer," The International Journal of Biochemistry & Cell Biology, 2005, vol. 37, pp. 1054-1065.
Gunduz, Mehmet et al., "Frequent deletion and down-regulation of ING4, a candidate tumor suppressor gene at 12p13, in head and neck squamous cell carcinomas," Gene, 2005, vol. 356, pp. 109-117.
Kim, Suwon, et al., "A screen for genes that suppress loss of contact inhibition: Identification of ING4 as a candidate tumor suppressor gene in human cancer," Proceedings of the National Academy of Sciences, 2004, vol. 101, No. 46, pp. 16251-16256.
Liu, Ta-Chiang et al., "Oncolytic HSV Armed with Platelet Factor 4, an antiangiogenic Agent, Shows Enhanced Efficacy," Molecular Therapy (online publication), 2006, pp. 1-9.
Ozer, Abdullah et al., "The candidate tumor suppressor ING4 represses activation of the hypoxia inducible factor (HIF)," Proceedings of the National Academy of Sciences, 2005, vol. 102, pp. 7481-7486.
Brown et al. (1994) Journal of General Virology 75:2367-2377, "Cell type and cell state determine differential in vitro growth of non-neurovirulent ICP34. 5-negative herpes simplex virus types 1 and 2".
Burton et al. (2001) Stem Cells 19:358-377, "Multiple Applications for Replication-Defective Herpes Simplex Virus Vectors".
He et al. (1998) Proc. Natl. Acad. Sci. 95:2509-2514, "A simplified system for generating recombinant adenoviruses".
Russell, et al. (2006) Experimental Cell Research 312:951-961, "Grow-ING, Age-ING and Die-ING: ING proteins link cancer, senescence and apoptosis".
Soliman et al. (2007) Trends in Biochemical Sciences 32(11):509-519, "After a decade of study-ING, a PHD for a versatile family of proteins".
Xie et al. (2008) Cancer Letters, doi:10.1016/j.canlet.2008.05.050, "Adenovirus-mediated ING4 expression suppresses lung carcinoma cell growth via induction of cell cycle alteration and apoptosis and inhibition of tumor invasion and angiogenesis".
Xie et al. (2009) Cancer Biotherapy and Radiopharmaceuticals 24(2):261-271, "Adenovirus-Mediated ING4 Expression Suppresses Pancreatic Carcinoma Cell Growth via Induction of Cell-Cycle Alteration, Apoptosis, and Inhibition of Tumor Angiogenesis".
Xie et al. (2011) Cancer Gene Therapy 18:176-188, "Enhanced antitumor activity by combining an adenovirus harboring ING4 with cisplatin for hepatocarcinoma cells".
Shah et al. (Journal of Neuro-Oncology 65: 203-226, 2003).
Unoki et al. (Journal of Biological Chemistry: 281: 34677-34686, 2006).

(Continued)

*Primary Examiner* — Mary E Mosher
(74) *Attorney, Agent, or Firm* — Swanson & Bratschun, L.L.C.

(57) ABSTRACT

A herpes simplex virus is disclosed in which the herpes simplex virus genome comprises a nucleic acid sequence encoding an ING4 polypeptide.

17 Claims, 5 Drawing Sheets

(56) References Cited

OTHER PUBLICATIONS

Yang et al. (2009) Chinese Journal of Cancer 28(11):27-34, "In vitro and in vivo inhibitory effect of Ad-ING4 gene on proliferation of human prostate cancer PC-3 cells".

Yang et al. (2011) Cancer Gene Therapy 18:176-188, "Enhanced antitumor activity by combining an adenovirus harboring ING4 with cisplatin for hepatocarcinoma cells".

Zhang et al. (2004) FEBS Letters 570:7-12, "ING4 induces G2/M cell cycle arrest and enhances the chemosensitivity to DNA-damage agents in HepG2 cells".

Shiseki, Masayuki et al., "p29ING4 and p28ING5 Bind to p53 and p300, and Enhance p53 Activity," Cancer Research, 2003, vol. 63, pp. 2373-2378.

Internatonal Search Report, prepared by the European Patent Office, acting as International Searching Authority, for international patent application No. PCT/GB2008/000527, completed Oct. 28, 2008, and mailed Nov. 13, 2008, 7 pages.

International Preliminary Report on Patentability, issued by the International Bureau of WIPO, for international patent application No. PCT/GB2008/000527, completed Aug. 19, 2009 and mailed Aug. 27, 2009, 10 pages.

* cited by examiner

Lanes       1  2  3  M

Lanes       1 2 3 4 5

SEQUENCE LISTING

<160> NUMBER OF SEQ ID NOS: 5

<210> SEQ ID NO 1
<211> LENGTH: 38
<212> TYPE: DNA
<213> ORGANISM: Artificial sequence
<220> FEATURE:
<223> OTHER INFORMATION: Synthetic sequence: Forward primer

<400> SEQUENCE: 1
gagaattcgc ggccgcgatg gctgcgggga tgtatttg                      38

<210> SEQ ID NO 2
<211> LENGTH: 38
<212> TYPE: DNA
<213> ORGANISM: Artificial sequence
<220> FEATURE:
<223> OTHER INFORMATION: Synthetic sequence: Reverse primer

<400> SEQUENCE: 2
agtctagact cgagctattt cttcttccgt tcttggga                      38

<210> SEQ ID NO 3
<211> LENGTH: 248
<212> TYPE: PRT
<213> ORGANISM: Homo sapiens

<400> SEQUENCE: 3

Met Ala Ala Gly Met Tyr Leu Glu His Tyr Leu Asp Ser Ile Glu Asn

```
              1               5              10              15
            Leu Pro Phe Glu Leu Gln Arg Asn Phe Gln Leu Met Arg Asp Leu Asp
                             20                  25                  30

Gln Arg Thr Glu Asp Leu Lys Ala Glu Ile Asp Lys Leu Ala Thr Glu
                         35                  40                  45

Tyr Met Ser Ser Ala Arg Ser Leu Ser Ser Glu Glu Lys Leu Ala Leu
                     50                  55                  60

Leu Lys Gln Ile Gln Glu Ala Tyr Gly Lys Cys Lys Glu Phe Gly Asp
            65                  70                  75                  80

Asp Lys Val Gln Leu Ala Met Gln Thr Tyr Glu Met Val Asp Lys His
                             85                  90                  95

Ile Arg Arg Leu Asp Thr Asp Leu Ala Arg Phe Glu Ala Asp Leu Lys
                            100                 105                 110

Glu Lys Gln Ile Glu Ser Ser Asp Tyr Asp Ser Ser Ser Lys Gly
                        115                 120                 125

Lys Lys Ser Arg Thr Gln Lys Glu Lys Ala Ala Arg Ala Arg Ser
            130                 135                 140

Lys Gly Lys Asn Ser Asp Glu Glu Ala Pro Lys Thr Ala Gln Lys Lys
            145                 150                 155                 160

Leu Lys Leu Val Arg Thr Ser Pro Glu Tyr Gly Met Pro Ser Val Thr
                            165                 170                 175

Phe Gly Ser Val His Pro Ser Asp Val Leu Asp Met Pro Val Asp Pro
                        180                 185                 190

Asn Glu Pro Thr Tyr Cys Leu Cys His Gln Val Ser Tyr Gly Glu Met
                    195                 200                 205

Ile Gly Cys Asp Asn Pro Asp Cys Ser Ile Glu Trp Phe His Phe Ala
                210                 215                 220

Cys Val Gly Leu Thr Thr Lys Pro Arg Gly Lys Trp Phe Cys Pro Arg
            225                 230                 235                 240

Cys Ser Gln Glu Arg Lys Lys Lys
                        245

<210> SEQ ID NO 4
<211> LENGTH: 1717
<212> TYPE: DNA
<213> ORGANISM: Homo sapiens

<400> SEQUENCE: 4
ccggggcgga tcggaagttg ctttgttttg cttcgagatg gctgcgggga tgtatttgga      60
acattatctg acagtattg aaaaccttcc ctttgaatta cagagaaact ttcagctcat     120
gagggaccta gaccaaagaa cagaggacct gaaggctgaa attgacaagt tggccactga     180
gtatatgagt agtgcccgca gcctgagctc gaggaaaaaa ttggcccttc tcaaacagat     240
ccaggaagcc tatggcaagt gcaaggaatt tggtgacgac aaggtgcagc ttgccatgca     300
gacctatgag atggtggaca acacattccg cggctggaca cagacctggg ccgttttga     360 ggctgatctc aaggagaaac agattgagtc aagtgactat gacagctctt ccagcaaagg     420
caaaaagagc cggactcaaa aggagaagaa agctgctcgt gctcgttcca agggaaaaa     480 ctcggatgaa gaagccccca agactgccca gaagaagtta agctcgtgc acaagtcc       540 tgagtatggg atgccctcag tgacctttgg cagtgtccac ccctctgatg tgttggatat     600
gcctgtggat cccaacgaac ccacctattg cctttgtcac caggtctcct atggagagat     660
gattggctgt gacaaccctg attgttccat tgagtggttc cattttgcct gtgtggggct     720
```

-continued

```
gacaaccaag cctcggggga aatggttttg cccacgctgc tcccaagaac ggaagaagaa    780
atagataagg gccttggatt ccaacacagt ttcttccaca tccccctgact tgggctagtg   840
ggcagaggaa tgcctgtgct ggggccaggg gttcagggag gagtggatgg cacagtgctg   900
tcatcccttc tcctccctc tccccactcc cggtgctgag gctgcatcag accctggtag    960
ggaggggtgc cgcagccact aacggtatgt gctctccttc agccctctcc cttcggaggg   1020
acgtggtctt gcccactgtc cttttgcctc catgctgagg tcggtgctgt atttcagagg   1080
gagggtcctt ttcattctcc ttgctttgta tttaaggact ggggcatagc atggggggcag  1140
tcccccagac ctcttcattc cccctcctgt ggtgagggct aggtgtgatc aacactttc    1200
ttctccattc ccttcctgct tttttcatgg tgggggatcc accaggtcat ctaggctctg   1260
gccctagttg aaggggcacc ccttcctctg tgccaagagg attcatcctg ggagaggggg   1320
caaggtggaa tgcagataac tcacatgtaa aaggaacttg ggtaggtaaa taaaagctat   1380
acatgttggc ctgctgtgtt tattgtagag acactgtttt agtaaacatg ctgagcattc   1440
attttgcgtc ctctgggttg gatgcaatgt gagaggatgg catgccagaa ttaggacacg   1500
acatgaaacc agagtggtgc ctctgtccga gaacttgtaa gttctcaact tgggaaagac   1560
agaggtgctg gagggtaggc ctcagaccag ggggtctcca aaactttgta aatcatgcat   1620
cttttctcca taaaacatct ttcacttaat ttccaataaa tgatgtattt gtgctataca   1680
tacgtactgc tatactataa aaaaaaaaaa aaaaaaa                            1717

<210> SEQ ID NO 5
<211> LENGTH: 747
<212> TYPE: DNA
<213> ORGANISM: Homo sapiens

<400> SEQUENCE: 5
atggctgcgg ggatgtattt ggaacattat ctggacagta ttgaaaacct tcccttttgaa   60
ttacagagaa actttcagct catgagggac ctagaccaaa gaacagagga cctgaaggct   120
gaaattgaca agttggccac tgagtatatg agtagtgccc gcagcctgag ctccgaggaa   180
aaattggccc ttctcaaaca gatccaggaa gcctatggca agtgcaagga atttggtgac   240
gacaaggtgc agcttgccat gcagacctat gagatggtgg acaaacacat tcggcggctg   300
gacacagacc tggcccgttt tgaggctgat ctcaaggaga aacagattga gtcaagtgac   360
tatgacagct cttccagcaa aggcaaaaag agccggactc aaaaggagaa gaaagctgct   420
cgtgctcgtt ccaaagggaa aaactcggat gaagaagccc caagactgc ccagaagaag    480
ttaaagctcg tgcgcacaag tcctgagtat gggatgccct cagtgacctt tggcagtgtc   540
caccccctctg atgtgttgga tatgcctgtg gatcccaacg aacccaccta ttgcctttgt   600
caccaggtct cctatggaga gatgattggc tgtgacaacc ctgattgttc cattgagtgg   660
ttccattttg cctgtgtggg gctgacaacc aagcctcggg ggaaatggtt ttgcccacgc   720
tgctcccaag aacggaagaa gaaatag                                      747
```

HERPES SIMPLEX VIRUSES AND METHODS OF VIRAL REPLICATION

CROSS-REFERENCE TO RELATED APPLICATIONS

This application is a Continuation of U.S. patent application Ser. No. 12/527,380 filed Aug. 14, 2009, now U.S. Pat. No. 8,163,292 which is a 35 USC §371 of PCT Application Serial No. PCT/GB2008/000527, filed Feb. 15, 2008, currently pending, entitled "Herpes Simplex Viruses and Methods of Viral Replication," which claims priority to Great Britain Patent Application No. 0703066.1, filed Feb. 16, 2007, entitled "Herpes Simplex Viruses and Methods of Viral Replication," and U.S. Patent Application No. 60/916,862, filed May 9, 2007.

FIELD OF THE INVENTION

The present invention relates to Herpes Simplex Viruses, methods for the replication of Herpes Simplex Virus and the use of Herpes Simplex Virus in the treatment of disease.

Incorporated by reference herein in its entirety is the Sequence Listing co-submitted with the instant application, entitled "6524532.txt", created Aug. 5, 2009, size of 7 kilobytes.

BACKGROUND

Inhibitor of New Growth 4 (ING 4) is a member of the Inhibitor of New Growth family of candidate tumour suppressor proteins of which 6 have been reported in humans (Garkavstev et al 1996). Loss of the ING4 gene has been reported in head and neck squamous cell carcinoma (Gunduz et al 2005) and in glioma (Garkavtsev et al 2004) and, although a number of different functions have been described for this protein, its precise mode of action is yet to be elucidated.

The ING gene products inhibit cell proliferation (Russell et al 2006, Campos et al., 2004, Shi and Gozani 2005) and their overexpression is associated with increased apoptosis (Nagashima et al., (2001). ING4 inhibition of cell proliferation is probably mediated by its binding to p53 and acetyltransferase p300 thus facilitating acetylation and activation of p53 (Shiseki et al. 2003). ING4 has been reported as a component of the HBO1 HAT complex required for normal cell cycle progression and the majority of histone H4 acetylation (Doyon et al, 2006) suggesting a role in chromatin remodelling and transcriptional regulation. The extensive loss of histone H4 acetylation during human cancer development strongly suggests a tumour suppressor role for ING4. ING4 has been shown to interact with the RelA subunit of NF-κB resulting in suppressed expression of angiogenesis-related genes such as IL-6, IL-8 and Cox-2 (Garkavtsev et al 2004) and its loss in glioma is associated with more aggressive tumour growth and vascularisation. Loss of tumour suppressor genes is a common feature of cancer progression. ING4 suppression in multiple myeloma cells in vitro resulted in increased expression of the pro-angiogenic IL-8 and osteopontin probably via increased activity of hypoxia inducible factor-1 (HIF-1), involved in up-regulating angiogenesis genes during hypoxia, and, in multiple myeloma patients, decreased levels of ING4 were associated with both high IL-8 production and microvascular density (Colla et al., 2007). ING4 repression of the HIF transcription factor, probably mediated via an interaction with HIF prolyl hydroxylase (HPH)-2, also involved in regulating angiogenesis genes, has also been reported (Ozer et al., 2005, Colla et al 2007).

Herpes Simplex Virus

The herpes simplex virus (HSV) genome comprises two covalently linked segments, designated long (L) and short (S). Each segment contains a unique sequence flanked by a pair of inverted terminal repeat sequences. The long repeat (RL or $R_L$) and the short repeat (RS or $R_S$) are distinct.

The HSV ICP34.5 (also γ34.5) gene, which has been extensively studied, has been sequenced in HSV-1 strains F and syn17+ and in HSV-2 strain HG52. One copy of the ICP34.5 gene is located within each of the RL repeat regions. Mutants inactivating both copies of the ICP34.5 gene (i.e. null mutants), e.g. HSV-1 strain 17 mutant 1716 (HSV 1716) or the mutants R3616 or R4009 in strain F, are known to lack neurovirulence, i.e. be avirulent (non-neurovirulent), and have utility as both gene delivery vectors or in the treatment of tumours by oncolysis. HSV-1 strain 17 mutant 1716 has a 759 bp deletion in each copy of the ICP34.5 gene located within the BamHI s restriction fragment of each RL repeat.

ICP34.5 null mutants such as HSV1716 are, in effect, first-generation oncolytic viruses. Most tumours exhibit individual characteristics and the ability of a broad spectrum first generation oncolytic virus to replicate in or provide an effective treatment for all tumour types is not guaranteed.

HSV 1716 is an oncolytic, non-neurovirulent HSV and is described in EP 0571410 and WO 92/13943. HSV 1716 has been deposited on 28 Jan. 1992 at the European Collection of Animal Cell Cultures, Vaccine Research and Production Laboratories, Public Health Laboratory Services, Porton Down, Salisbury, Wiltshire, SP4 0JG, United Kingdom under accession number V92012803 in accordance with the provisions of the Budapest Treaty on the International Recognition of the Deposit of Microorganisms for the Purposes of Patent Procedure (herein referred to as the 'Budapest Treaty').

SUMMARY OF THE INVENTION

It has now been found that herpes simplex virus comprising nucleic acid encoding an ING4 polypeptide has an enhanced ability to retard tumour growth. In particular, the inventors created a variant herpes simplex virus comprising nucleic acid encoding ING4 polypeptide and investigated the effect of administering this variant to mice with tumour implants. They found that the survival time of mice receiving the herpes simplex virus variant was significantly improved compared to control, and in addition, the mice receiving the variant had significantly smaller average tumour volumes. These results demonstrate that the ING4 polypeptide enhances herpes simplex virus-mediated oncolysis.

One possible explanation for these observations is that the ING4 polypeptide inhibits angiogenesis, thereby reducing the rate at which the tumour can grow. Thus, this mechanism may synergistically interact with the oncolytic ability of herpes simplex virus to provide an improved tumour cell-killing ability.

However, whilst conducting further investigations the inventors unexpectedly found that tumour cells infected with the herpes simplex virus variant comprising nucleic acid encoding ING4 had a significantly higher output of progeny virions both in vivo and in vitro compared to control. Further experiments showed that cells constitutively expressing an ING4 polypeptide and infected with wild-type herpes simplex virus also had a higher output of progeny virions compared to control. This indicates that ING4 expression confers a growth advantage on herpes simplex virus.

These results provide the basis for a new approach for improving efficacy of treatments involving administration of herpes simplex virus. In particular, these results have the potential to lead to much needed new and improved treatments for cancer and other conditions.

HSV1716ING4 has been deposited in the name of Crusade Laboratories Limited having an address at PO Box 1716, Glasgow, G51 4WF, United Kingdom, at the European Collection of Cell Cultures (ECACC), Health Protection Agency, Porton Down, Salisbury, Wiltshire, SP4 0JG, United Kingdom in accordance with the provisions of the Budapest Treaty on the International Recognition of the Deposit of Microorganisms for the Purposes of Patent Procedure (herein referred to as the 'Budapest Treaty').

In a broad aspect, the present invention relates to an herpes simplex virus wherein the herpes simplex virus genome comprises nucleic acid encoding an anti-angiogenic polypeptide or protein. In other broad aspects, the invention relates to an herpes simplex virus wherein the herpes simplex virus genome comprises nucleic acid encoding a polypeptide that enhances replication efficiency of the herpes simplex virus. The anti-angiogenic polypeptide may be a polypeptide that enhances HSV replication efficiency.

The anti-angiogenic polypeptide or protein, or polypeptide that enhances HSV replication efficiency, is preferably heterologous to the HSV, i.e. not being normally encoded or expressed by the corresponding wild type HSV. More preferably, the anti-angiogenic polypeptide or protein, or polypeptide that enhances HSV replication efficiency, is a mammalian polypeptide or protein. Still more preferably it is a candidate tumor suppressor gene. The HSV is preferably capable of expressing the anti-angiogenic polypeptide or polypeptide that enhances HSV replication efficiency. The anti-angiogenic polypeptide or polypeptide that enhances HSV replication efficiency is preferably an ING4 polypeptide.

More particularly, the present invention concerns HSV capable of expressing ING4 and the use of ING4 in improving the replication efficiency of HSV.

Accordingly, in one aspect, the present invention relates to a herpes simplex virus, wherein the herpes simplex virus genome comprises a nucleic acid sequence encoding an anti-angiogenic polypeptide. In a preferred embodiment the anti-angiogenic polypeptide is ING4. The herpes simplex virus may also be non-neurovirulent.

In a further aspect, the present invention relates to a herpes simplex virus wherein the herpes simplex virus genome comprises a nucleic acid sequence encoding an ING4 polypeptide. The herpes simplex virus may be non-neurovirulent.

The HSV may be an oncolytic HSV. HSV, e.g. oncolytic HSV, that may be used in the invention include HSV in which one or both of the γ34.5 (also called ICP34.5) genes are modified (e.g. by mutation which may be a deletion, insertion, addition or substitution) such that the respective gene is incapable of expressing, e.g. encoding, a functional ICP34.5 protein. Preferably, in HSV according to the invention both copies of the γ34.5 gene are modified such that the modified HSV is not capable of expressing, e.g. producing, a functional ICP34.5 protein. The viruses, e.g. oncolytic viruses, are preferably non-neurovirulent.

In certain arrangements the herpes simplex virus may be a gene specific null mutant, such as an ICP34.5 null mutant. Where all copies of the ICP34.5 gene present in the herpes simplex virus genome (two copies are normally present) are disrupted such that the herpes simplex virus is incapable of producing a functional ICP34.5 gene product, the virus is considered to be an ICP34.5 null mutant. In other arrangements the herpes simplex virus may lack at least one expressible ICP34.5 gene. In another arrangement the herpes simplex virus may lack only one expressible ICP34.5 gene. In other arrangements the herpes simplex virus may lack both expressible ICP34.5 genes. In still other arrangements each ICP34.5 gene present in the herpes simplex virus may not be expressible. Lack of an expressible ICP34.5 gene means, for example, that expression of the ICP34.5 gene does not result in a functional ICP34.5 gene product.

The genome of the HSV according to the invention is further modified to contain nucleic acid encoding at least one copy of an anti-angiogenic polypeptide such that the polypeptide can be expressed from the nucleic acid. The nucleic acid encoding the polypeptide may be located in at least one RL1 locus of the herpes simplex virus. For example, the nucleic acid may be located in or overlap at least one of the ICP34.5 protein coding sequences of the herpes simplex virus genome. This provides a convenient way of inactivating the ICP34.5 gene, thereby providing non-neurovirulence.

The anti-angiogenic polypeptide or polypeptide that enhances replication efficiency may be a selected ING4 polypeptide. As such, in a preferred embodiment the modified HSV is an expression vector capable of expressing the anti-angiogenic polypeptide or protein, or HSV polypeptide that enhances replication efficiency (e.g. ING4) upon infection of cells, preferably mammalian cells. In another preferred embodiment, the HSV is an oncolytic expression vector.

In order to effect expression of the anti-angiogenic polypeptide or polypeptide that enhances replication efficiency (e.g. ING4) the nucleic acid encoding the polypeptide is preferably operably linked to a regulatory sequence, e.g. a promoter, capable of effecting transcription of the nucleic acid encoding the polypeptide. A regulatory sequence (e.g. promoter) that is operably linked to a nucleotide sequence may be located adjacent to that sequence or in close proximity such that the regulatory sequence can effect and/or control expression of a product of the nucleotide sequence. The encoded product of the nucleotide sequence may therefore be expressible from that regulatory sequence.

In this specification the term "operably linked" may include the situation where a selected nucleotide sequence and regulatory nucleotide sequence are covalently linked in such a way as to place the expression of a nucleotide sequence under the influence or control of the regulatory sequence. Thus a regulatory sequence is operably linked to a selected nucleotide sequence if the regulatory sequence is capable of effecting transcription of a nucleotide sequence which forms part or all of the selected nucleotide sequence. Where appropriate, the resulting transcript may then be translated into a desired protein or polypeptide.

Nucleic acid vectors useful for generating herpes simplex viruses of the present invention are described, for example, on page 41 line 19 to page 55 line 30 of WO 2005/049845. This is incorporated herein by reference. One such vector provided by the inventors is plasmid RL1.dIRES-GFP deposited in the name of Crusade Laboratories Limited at the European Collection of Cell Cultures (ECACC), Health Protection Agency, Porton Down, Salisbury, Wiltshire, SP4 0JG, United Kingdom on 3 Sep. 2003 under accession number 03090303 in accordance with the provisions of the Budapest Treaty.

The nucleic acid sequence encoding the ING4 polypeptide may form part of a nucleic acid cassette which is inserted in the genome of a selected herpes simplex virus by homologous recombination. Whether part of a cassette or not, the site of insertion may be in any genomic location selected. One preferred insertion site is in one or both of the long repeat regions ($R_L$), and one copy of the cassette is preferably inserted in each copy of the long repeat ($R_L$). More preferably the insertion site is in at least one (preferably both) RL1 locus and most preferably it is inserted in at least one (preferably both) of the ICP34.5 protein coding sequences of the HSV genomic DNA. It is preferred that the insertion occurs in identical or substantially similar positions in each of the two repeat regions, RL1 loci or ICP34.5 protein coding sequences.

Insertion may be such as to produce a modified virus which is a non-neurovirulent mutant capable of expressing the encoded ING4 polypeptide upon transfection into mammalian, more preferably human, cells in vivo and in vitro. The non-neurovirulent mutant may be an ICP34.5 null mutant.

The nucleic acid cassette may be of any size, e.g. up to 5, 10, 15, 20, 25, 30, 35, 40, 45 or 50 kbp in length.

HSV according to the invention are provided for use in medical treatment of disease, more particularly in the treatment of a cancerous condition. A method of treatment of a cancerous condition is provided comprising the step of administering an HSV according to the invention to an individual in need of such treatment, e.g. in a therapeutically effective amount. HSV according to the invention are also provided for use in the manufacture of a medicament for the treatment of a cancerous condition. HSV according to the invention are also provided for use in treatment of a tumour, e.g. oncolytic treatment of a tumour.

A medicament, pharmaceutical composition or vaccine comprising an herpes simplex virus according to the present invention is also provided which may comprise an HSV according to the present invention together with a pharmaceutically acceptable carrier, adjuvant or diluent.

The herpes simplex virus of the invention may be derived from any HSV including any laboratory strain or clinical isolate (non-laboratory strain) of HSV. Preferably the HSV is a mutant of HSV-1 or HSV-2. Alternatively the HSV may be an intertypic recombinant of HSV-1 and HSV-2. The mutant may be of one of laboratory strains HSV-1 strain 17, HSV-1 strain F or HSV-2 strain HG52. The mutant may be of the non-laboratory strain JS-1. Preferably the mutant is a mutant of HSV-1 strain 17. The herpes simplex virus may be a further mutant of one of HSV-1 strain 17 mutant 1716, HSV-1 strain F mutant R3616, HSV-1 strain F mutant G207, HSV-1 mutant NV1020. Preferably the herpes simplex virus is a further mutant of one of HSV-1 strain 17 mutant 1716.

Herpes simplex viruses of the invention may be used in 'gene delivery' methods in vitro or in vivo. Non-neurovirulent herpes simplex viruses of the invention are expression vectors and may be used to infect selected cells or tissues in order to express the anti-angiogenic polypeptide or protein, or polypeptide that enhances HSV replication efficiency (e.g. ING4) encoded by the herpes simplex virus genome.

In one arrangement, cells may be taken from a patient, a donor or from any other source, infected with a herpes simplex virus of the invention, optionally screened for expression and/or function of the encoded ING4, and optionally returned/introduced to a patient's body, e.g. by injection.

Delivery of herpes simplex viruses of the invention to the selected cells may be performed using naked virus or by encapsulation of the virus in a carrier, e.g. nanoparticles, liposomes or other vesicles.

In vitro cultured cells, preferably human or mammalian cells, transformed with viruses of the present invention and preferably cells expressing the ING4 polypeptide as well as methods of transforming such cells in vitro with said viruses form further aspects of the present invention.

The HSV genome may contain additional mutations and/or heterologous nucleotide sequences. Additional mutations may include disabling mutations, which may affect the virulence of the virus or its ability to replicate. For example, mutations may be made in any one or more of ICP6, ICP0, ICP4, ICP27. Preferably, a mutation in one of these genes (optionally in both copies of the gene where appropriate) leads to an inability (or reduction of the ability) of the HSV to express the corresponding functional polypeptide. By way of example, the additional mutation of the HSV genome may be accomplished by addition, deletion, insertion or substitution of nucleotides.

The cancerous condition may be any unwanted cell proliferation (or any disease manifesting itself by unwanted cell proliferation), neoplasm or tumour or increased risk of or predisposition to the unwanted cell proliferation, neoplasm or tumour. The cancerous condition may be a cancer and may be a benign or malignant cancer and may be primary or secondary (metastatic). A neoplasm or tumour may be any abnormal growth or proliferation of cells and may be located in any tissue. Examples of tissues include the colon, pancreas, lung, breast, uterus, stomach, kidney, testis, central nervous system (including the brain), peripheral nervous system, skin, blood or lymph.

Cancer/tumour types which may be treated may be primary or secondary (metastatic) tumours. Tumours to be treated may be nervous system tumours originating in the central or peripheral nervous system, e.g. glioma, medulloblastoma, meningioma, neurofibroma, ependymoma, Schwannoma, neurofibrosarcoma, astrocytoma and oligodendroglioma, or may be non-nervous system tumours originating in non-nervous system tissue e.g. melanoma, mesothelioma, lymphoma, hepatoma, epidermoid carcinoma, prostate carcinoma, breast cancer cells, lung cancer cells or colon cancer cells. HSV mutants of the present invention may be used to treat metastatic tumours of the central or peripheral nervous system which originated in a non-nervous system tissue. For example, cancerous conditions that may be treated by the invention include squamous cell carcinomas, ovarian tumours/carcinomas, hepatocellular carcinomas, and breast adenocarcinomas.

In this specification, non-neurovirulence is defined by the ability to introduce a high titre of virus (approx $10^6$ plaque forming units (pfu)) to an animal or patient without causing a lethal encephalitis such that the $LD_{50}$ in animals, e.g. mice, or human patients is in the approximate range of $\geq 10^6$ pfu.

The patient to be treated may be any animal or human. The patient may be a non-human mammal, but is more preferably a human patient. The patient may be male or female.

The invention also provides a method of lysing or killing tumour cells in vitro or in vivo comprising the step of administering to the cells an herpes simplex virus of the invention.

The invention also provides a method of expressing in vitro or in vivo an ING4 polypeptide, said method comprising the step of infecting at least one cell or tissue of interest with a herpes simplex virus of the invention.

In a further aspect, the invention relates to an in vivo or in vitro method of increasing replication efficiency of a herpes simplex virus in a cell infected with herpes simplex virus, comprising the step of causing the cell to express a nucleic acid sequence encoding an ING4 polypeptide.

The increase in replication may be an increase in the amount of virions produced by the cell, e.g. an increase in HSV yield. The increase in HSV replication efficiency may be relative to control, e.g. relative to a cell that expresses ING4 at wild-type levels. The step of causing, e.g. stimulating, the cell to express a nucleic acid sequence encoding an ING4 polypeptide may comprise causing and/or effecting an increase in the concentration of ING4 polypeptide in the cell, e.g. relative to control. For example, the method may comprise increasing expression of nucleic acid encoding ING4 polypeptide. This may be achieved by introducing into the cell a heterologous construct comprising the nucleic acid sequence encoding an ING4 polypeptide, e.g. the term heterologous meaning that the construct is not normally present in the wild-type cell. The nucleic acid sequence encoding an ING4 polypeptide may be operably linked to a regulatory nucleotide sequence, wherein said regulatory nucleotide sequence has a role in controlling transcription of the ING4 polypeptide. Expression of the nucleic acid encoding ING4 may be constitutive.

The presence of ING4 in a cell (at levels above the endogenous level of ING4 normally present in the cell type) infected with HSV can lead to an increase in replication efficiency of the HSV. This may result in a greater yield of HSV virions from the infected cell(s). Replication efficiency can be measured by comparing the number of virions produced by cells infected with HSV and in which excess ING4 (i.e. ING4 additional to that normally present because of endogenous expression) is present with control cells infected with the same HSV but in which excess ING4 is not present, i.e. control cells are infected with the same HSV but do not produce ING4 polypeptide above the normal endogenous level. One may optionally determine a value for the number of HSV virions produced per pfu of HSV infected for cells in which ING4 is and is not present. An increase in replication efficiency is present where cells in which excess ING4 is present show an increase, preferably a statistically significant increase, in the amount of HSV virions produced compared to the control. The increase in replication efficiency may lead to production level of virions that is 1.1, 1.2, 1.3, 1.4, 1.5, 2, 3, 4, 5, 6, 7, 8, 9, 10, 20, 30, 40, 50, 60, 70, 80, 90, 100, 200, 300, 400, 500, 600, 700, 800, 900 or 1000 (or more) times that of the control.

The cell may be any cell that is capable of being infected with HSV, but is preferably a tumour cell, e.g. tumour cells capable of being lysed by HSV, e.g. squamous cell carcinoma, ovarian tumour, human breast adenocarcinoma, ovarian carcinoma and hepatocellular carcinoma.

In a further aspect the invention provides a cell, in vivo or in vitro, infected with a herpes simplex virus, which cell comprises a heterologous construct comprising nucleic acid sequence encoding an ING4 polypeptide. Expression of the nucleic acid encoding ING4 may be constitutive.

In a further aspect the invention provides a nucleic acid encoding an ING4 polypeptide for use in a therapeutic method, which method comprises administering a non-neurovirulent herpes simplex virus to a patient in need of treatment. In a further aspect, the invention provides a non-neurovirulent herpes simplex virus for use in a therapeutic method, which method comprises administering a nucleic acid encoding ING4 to patient in need of treatment.

In a further aspect the invention provides use of a nucleic acid encoding an ING4 polypeptide in the manufacture of a medicament for a therapeutic method, which method comprises administering a non-neurovirulent herpes simplex virus to patient in need of treatment. In a further aspect the invention provides use of a non-neurovirulent herpes simplex virus in the manufacture of a medicament for a therapeutic method, which method comprises administering a nucleic acid encoding ING4 to patient in need of treatment.

In a further aspect the invention provides a method of treating a patient comprising administering to the patient a non-neurovirulent herpes simplex virus and a nucleic acid encoding an ING4 polypeptide.

The patient in need of treatment may be a patient with a cancerous condition. The treatment may be treatment of cancer and/or tumour.

Nucleic acid encoding an ING4 polypeptide for use in methods of treatment may be provided in a vector. The vector may be a gene therapy vector, e.g. it may enter cells of the patient upon administration. For example, the vector may be a virus vector, e.g. it may be a non-oncolytic HSV.

In further aspect the invention provides a composition comprising a herpes simplex virus and a nucleic acid encoding an ING4 polypeptide and/or an ING4 polypeptide. The composition may, for example, be a pharmaceutical composition comprising a non-neurovirulent herpes simplex virus and a nucleic acid encoding an ING4 polypeptide.

The inventors have shown that introduction of excess ING4 polypeptide to a cell (i.e. additional ING4 beyond that normally expressed by the cell) leads to increased levels of expression of wild type and mutant HSV. Accordingly, the present invention provides a method of replicating HSV in vitro or in vivo comprising (i) providing a cell or cell(s) having excess ING 4 and (ii) contacting the cell(s) with HSV capable of infecting the cell(s). For in vitro production of HSV via replication in infected cells this approach may lead to significant improvements in replication of HSV and enable higher viral titres to be obtained. The method may comprise the step of causing the cell(s) to express a nucleic acid sequence encoding an ING4 polypeptide. This may comprise the step of introducing into the cell(s) a heterologous construct comprising a nucleic acid sequence encoding an ING4 polypeptide.

Excess ING4 may be introduced to cells by causing the cell to express ING4 from a vector transfected into the cell, e.g. expression of recombinant ING4 from an expression vector. The vector may be an HSV such as HSV1716ING4 but may also be any suitable expression vector, e.g. plasmid vector. Additionally or alternatively the cell may be caused to overexpress endogenous ING4, e.g. through regulation or enhancement of the corresponding promoter. Additionally or alternatively the cell may be contacted with ING4 polypeptide, which for example may be obtained as recombinant ING4, e.g. through fermentation of bacteria transfected with an expression vector encoding ING4.

Accordingly, a further aspect of the present invention provides a method of replicating herpes simplex virus in cells infected with herpes simplex virus comprising contacting the cell with ING4 polypeptide. In a further aspect the invention provides a method of replicating herpes simplex virus in cells infected with herpes simplex virus comprising contacting the cell with a nucleic acid vector encoding ING4 and causing the cell to express ING4.

In accordance with the above, in yet a further aspect a method is provided for the in vitro replication of HSV comprising the steps of (i) providing a cell or cells with excess ING4, (ii) infecting the cell(s) with HSV, (iii) culturing the cell(s) in vitro, and (iv) harvesting viral progeny from the cell(s).

The HSV may be any HSV as described herein.

The cells may be any cells capable of infection by HSV and in which HSV can replicate. They may be in vitro cultured cells. They may be human or non-human cells. For example they may be from rabbit, guinea pig, rat, mouse or other rodent (including cells from any animal in the order Rodentia), cat, dog, pig, sheep, goat, cattle, horse, non-human primate or other non-human vertebrate organism; and/or non-human mammalian cells; and/or human cells.

In a further aspect of the invention, the invention provides HSV1716ING4, which has been deposited with the ECACC (European Collection of Cell Cultures, address Health Protection Agency, Porton Down, Salisbury, Wiltshire SP4 0JG, United Kingdom, in accordance with the Budapest Treaty on Feb. 15, 2008 under accession no. 08021501.

ING4

Reference to ING4 in this specification includes reference to the ING4 polypeptide having the amino acid sequence described under Accession no. NM_016162 GI:38201669 in the NCBI database at ncbi.nlm.nih.gov. Reference to ING4 also includes reference to isoforms, homologues and derivatives of ING4. Derivatives may comprise natural variations or polymorphisms which may exist between individuals or between members of a family. There are many homologues of ING4 polypeptide deposited in the Genbank database. For example a Blast search of the database identified around one hundred homologues. Homologues include, for example, other human ING4 isoforms such as BC007781, *Mus musculus* ING4 (e.g. NP_579923.1), *Cannis familiaris* ING4 (XP_534907.2), *Rattus norvegicus* (NP_001073356.1), *Pan troglodytes* ING4 (XP_001169091.1), *Equus caballus* (XP_001496617.1), *Gallus gallus* ING4 (NP_001006241.1), *Macaca mulatta* (XP_001118270.1), *Monodelphis domestica* (XP_001365016.1), *Bos Taurus* (NP_001030466.1), *Danio rerio* ((NP_001018304.1), *Xonpus laevis* (NP_001088224.1). The ING4 polypeptide or protein to which the invention relates is preferably a human ING4.

All such homologues and derivatives are included within the scope of the invention. Purely as examples, conservative replacements which may be found in such polymorphisms may be between amino acids within the following groups:
(i) alanine, serine, threonine;
(ii) glutamic acid and aspartic acid;
(iii) arginine and leucine;
(iv) asparagine and glutamine;
(v) isoleucine, leucine and valine;
(vi) phenylalanine, tyrosine and tryptophan.

In particular, peptides and polypeptides having a sequence identity of at least 70%, more preferably one of 75%, 80%, 85%, 90%, 95%, 96%, 97%, 98%, 99% and 100% with the amino acid sequence of ING4 set out under Accession no. NM_016162 GI:38201669 are included as ING4 polypeptides for the purposes of this specification. Nucleic acid sequences encoding any one of these ING4 polypeptides may be used for the purposes of ING4 expression in accordance with this invention.

Nucleic acid encoding an ING4 polypeptide may be selected by its ability to hybridise to the nucleic acid of SEQ ID NO: 4 or SEQ ID NO: 5 under high stringency conditions.

The ING4 polypeptide may be a polypeptide whose presence in a cell infected with herpes simplex virus leads to an increase in replication efficiency of the herpes simplex virus in said cell. In particular, the ING4 polypeptide may be a polypeptide whose presence in a cell infected with herpes simplex virus strain 17 or 1716 leads to an increase in replication efficiency of herpes simplex virus strain 17 or 1716 in said cell.

For example, an increase in expression of the nucleic acid sequence encoding the ING4 polypeptide in a cell infected with a herpes simplex virus leads to an increase in replication efficiency of the herpes simplex virus. As described above, an increase in replication efficiency, e.g. a greater replication efficiency, means, for example, that the cell produces a greater number of progeny virions, e.g. the yield of HSV particles from the cell is greater. The increase in replication efficiency may be relative to control, e.g. relative to a cell which expresses endogenous levels, or does not express, ING4. For example, where the HSV genome comprises nucleic acid encoding ING4 polypeptide, the increase in HSV replication efficiency may be relative to the same cell infected with the corresponding HSV that does not comprise nucleic acid encoding ING4 polypeptide.

The HSV may be strain 17 or strain 1716. Preferably the increase in replication efficiency is statistically significant, e.g. $p<0.05$, e.g. as determined using the Student's t-test or analysis of variance (ANOVA).

The increase in expression may be increase in expression in a cell line selected from the group consisting of: BHK, A431 human squamous cell carcinoma, CP70 human ovarian tumour, MDA-MB-468 human breast adenocarcinoma, Ovcar 3 human ovarian carcinoma and HuH7 human hepatocellular carcinoma. The experiments in Example 2 set out a suitable procedure to compare replication efficiency. For example, tumour cells may be infected with 1000 pfu for 72 hours.

The ING4 nucleotide sequence may encode a full length transcript or polypeptide (i.e. comprise the complete ING4 protein coding sequence). Alternatively, provided the polypeptide product retains ING4 activity, e.g. increased HSV replication efficiency, the ING4 nucleotide sequence may comprise one or more fragments of the full length sequence respectively coding for a fragment of the full length transcript or a truncated polypeptide.

A fragment may comprise a nucleotide sequence encoding at least 10% of the corresponding full length sequence, more preferably the fragment comprises at least 20, 30, 40, 50, 60, 70, 80, 85, 90, 95, 96, 97, 98 or 99% of the corresponding full length sequence. Preferably, the fragment comprises at least, i.e. has a minimum length of, 20 nucleotides, more preferably at least 30, 40, 50, 100, 150, 200, 300, 400, 500, 600, 700, 800, 900, 1000, 1100, 1200, 1300, 1400, 1500, 1600, 1700, 1800, 1900 or 2000 nucleotides. The fragment may have a maximum length, i.e. be no longer than, 20 nucleotides, more preferably no longer than 30, 40, 50, 100, 150, 200, 300, 400, 500, 600, 700, 800, 900, 1000, 1100, 1200, 1300, 1400, 1500, 1600, 1700, 1800, 1900 or 2000 nucleotides. The fragment length may be anywhere between said minimum and maximum length.

In one preferred arrangement, the herpes simplex virus is HSV1716ING4 deposited in the name of Crusade Laboratories Limited having an address at PO Box 1716, Glasgow, G51 4WF, United Kingdom, at the European Collection of Cell Cultures (ECACC), Health Protection Agency, Porton Down, Salisbury, Wiltshire, SP4 0JG, United Kingdom in accordance with the provisions of the Budapest Treaty.

The amino acid and nucleotide sequences for human ING4 as set out under Accession no. NM_016162.2 GI:38201669 of the NCBI database are reproduced below as SEQ ID No. 3 and SEQ ID No.4.

Amino Acid Sequence:

[SEQ ID No. 3]

MAAGMYLEHYLDSIENLPFELQRNFQLMRDLDQRTEDLKAEIDKLATEYM

SSARSLSSEEKLALLKQIQEAYGKCKEFGDDKVQLAMQTYEMVDKHIRRL

DTDLARFEADLKEKQIESSDYDSSSSKGKKSRTQKEKKAARARSKGKNSD

EEAPKTAQKKLKLVRTSPEYGMPSVTFGSVHPSDVLDMPVDPNEPTYCLC

HQVSYGEMIGCDNPDCSIEWFHFACVGLTTKPRGKWFCPRCSQERKKK

Nucleotide Sequence:

[SEQ ID No. 4]

```
   1  ccggggcgga tcggaagttg ctttgttttg cttcgagatg
      gctgcgggga tgtatttgga
  61  acattatctg gacagtattg aaaaccttcc ctttgaatta
      cagagaaact ttcagctcat
 121  gagggaccta gaccaaagaa cagaggacct gaaggctgaa
      attgacaagt tggccactga
 181  gtatatgagt agtgcccgca gcctgagctc cgaggaaaaa
      ttggcccttc tcaaacagat
 241  ccaggaagcc tatggcaagt gcaaggaatt tggtgacgac
      aaggtgcagc ttgccatgca
 301  gacctatgag atggtggaca aacacattcg gcggctggac
      acagacctgg cccgttttga
 361  ggctgatctc aaggagaaac agattgagtc aagtgactat
      gacagctctt ccagcaaagg
 421  caaaaagagc cggactcaaa aggagaagaa agctgctcgt
      gctcgttcca aagggaaaaa
 481  ctcggatgaa gaagccccca agactgccca gaagaagtta
      aagctcgtgc gcacaagtcc
 541  tgagtatggg atgccctcag tgacctttgg cagtgtccac
      ccctctgatg tgttggatat
 601  gcctgtggat cccaacgaac ccacctattg cctttgtcac
      caggtctcct atggagagat
 661  gattggctgt gacaaccctg attgttccat tgagtggttc
      cattttgcct gtgtggggct
 721  gacaaccaag cctcggggga aatggttttg cccacgctgc
      tcccaagaac ggaagaagaa
 781  atagataagg gccttggatt ccaacacagt ttcttccaca
      tcccctgact tgggctagtg
 841  ggcagaggaa tgcctgtgct ggggccaggg gttcagggag
      gagtggatgg cacagtgctg
 901  tcatcccttc tcctcccctc tcccactcc cggtgctgag
      gctgcatcag accctggtag
 961  ggaggggtgc cgcagccact aacggtatgt gctctccttc
      agccctctcc cttcggaggg
1021  acgtggtctt gcccactgtc cttttgcctc catgctgagg
      tcggtgctgt atttcagagg
1081  gagggtcctt ttcattctcc ttgctttgta tttaaggact
      ggggcatagc atggggcag
1141  tcccccagac ctcttcattc ccctcctgt ggtgagggct
      aggtgtgatc aacactttc
1201  ttctccattc ccttcctgct tttttcatgg tgggggatcc
      accaggtcat ctaggctctg
1261  gccctagttg aaggggcacc ccttcctctg tgccaagagg
      attcatcctg ggagagggg
1321  caaggtggaa tgcagataac tcacatgtaa aaggaacttg
      ggtaggtaaa taaaagctat
1381  acatgttggc ctgctgtgtt tattgtagag acactgtttt
      agtaaacatg ctgagcattc
1441  attttgcgtc ctctgggttg gatgcaatgt gagaggatgg
      catgccagaa ttaggacacg
1501  acatgaaacc agagtggtgc ctctgtccga gaacttgtaa
      gttctcaact tgggaaagac
1561  agaggtgctg gagggtaggc ctcagaccag ggggtctcca
      aaactttgta aatcatgcat
1621  cttttctcca taaaacatct ttcacttaat ttccaataaa
      tgatgtattt gtgctataca
1681  tacgtactgc tatactataa aaaaaaaaaa aaaaaaa
```

The 747 bp cDNA sequence encoding human ING4 (SEQ ID No.5) is found between positions 38-784 (inclusive) in SEQ ID No.4.

Herpes Simplex Viruses

In this specification a herpes simplex virus (HSV) may be any herpes simplex virus. Suitable HSV include any laboratory strain or clinical isolate (non-laboratory strain) of HSV. Preferably the HSV is an HSV-1 or HSV-2. Alternatively the HSV may be an intertypic recombinant of HSV-1 and HSV-2. The HSV may be one of laboratory strains HSV-1 strain 17, HSV-1 strain F or HSV-2 strain HG52. The HSV may be the non-laboratory strain JS-1. Preferably the HSV is HSV-1 strain 17 or a mutant thereof. The HSV may be a further mutant of one of HSV-1 strain 17 mutant 1716, HSV-1 strain F mutant R3616, HSV-1 strain F mutant G207, HSV-1 mutant NV1020.

The parent herpes simplex virus, from which a virus of the invention is derived may be of any kind, e.g. HSV-1 or HSV-2. In one preferred arrangement the herpes simplex virus is a variant of HSV-1 strain 17 and may be obtained by modification of the strain 17 genomic DNA. Suitable modifications include the insertion of the nucleic acid sequence encoding the angi-angiogenic polypeptide or polypeptide that enhances replication efficiency into the herpes simplex virus genomic DNA. The insertion may be performed by homologous recombination of the exogenous nucleic acid sequence into the genome of the selected herpes simplex virus.

Although the non-neurovirulent phenotype of the herpes simplex virus of the invention may be the result of insertion of the nucleic acid sequence in the RL1 locus, herpes simplex viruses according to the present invention may be obtained by utilising a non-neurovirulent parent strain, e.g. HSV1716 deposited under the Budapest Treaty at the European Collection of Animal Cell Cultures (ECACC), Health Protection Agency, Porton Down, Salisbury, Wiltshire, United Kingdom under accession number V92012803, and inserting the nucleic acid sequence at another location of the genome by standard genetic engineering techniques, e.g. homologous recombination. In this aspect the location of the herpes simplex virus genome selected for insertion of the ING4 nucleic acid sequence or cassette containing said sequence may be a neutral location.

Herpes simplex viruses of the present invention may be variants of a known 'parent' strain from which the herpes simplex virus of the invention has been derived. A particularly preferred parent strain is HSV-1 strain 17. Other parent strains may include HSV-1 strain F or HSV-2 strain HG52 or any of the laboratory or non-laboratory strains described above or any other HSV. A variant comprises an HSV in which the genome substantially resembles that of the parent, contains the nucleic acid sequence and may contain a limited number of other modifications, e.g. one, two, three, four, five or less than ten other specific mutations, which may be introduced to disable the pathogenic properties of the herpes simplex virus, for example a mutation in the ribonucleotide reductase (RR) gene, the 65K trans inducing factor (TIF) and/or a small number of mutations resulting from natural variation, which may be incorporated naturally during replication and selection in vitro or in vivo. Otherwise the genome of the variant will be that of the parent strain.

For example, in some embodiments the herpes simplex virus genome may, have a mutation in the ICP34.5 gene and the ribonucleotide reductase gene, e.g. the ICP34.5 and ribonucleotide reductase genes may not produce a functional product, but the genome may otherwise substantially resemble the genome of HSV-1 strain 17 or F or HSV-2 strain HG52. In other embodiments the herpes simplex virus genome may have a mutation in the ICP34.5 gene and ribonucleotide reductase gene, e.g. the ICP34.5 and ribonucleotide reductase gene may not produce a functional product, but the genome may otherwise be the genome of HSV-1 strain 17 or F or HSV-2 strain HG52. The term "substantially resembles" may mean that the herpes simplex virus genome is 70, 75, 80, 85, 90, 95, 96, 97, 98, 99, 99.9 or 99.99% identical to the genome of HSV-1 strain 17 or F or HSV-2 strain HG52.

The herpes simplex virus of the present invention is preferably a mutant herpes simplex virus. A mutant herpes simplex virus is a non-wild type herpes simplex virus and may be a recombinant herpes simplex virus. Mutant herpes simplex viruses may comprise a genome containing modifications relative to the wild type. A modification may include at least one deletion, insertion, addition or substitution.

As described above, the herpes simplex virus may be a laboratory HSV strain or a non-laboratory strain. The laboratory strain may be, for example, HSV-1 strain 17, or F, or HSV-2 strain HG52. Laboratory strains may optionally be serially passaged HSV strains, e.g. a strain that has been serially passaged at least 100, 200, 500, 1000, or 10000 times. A non-laboratory strain may be a clinical isolate, e.g. a recent clinical isolate. A laboratory strain is, for example, not a recent clinical isolate.

Sequence Identity

Percentage (%) sequence identity is defined as the percentage of amino acid residues in a candidate sequence that are identical with residues in the given listed sequence (referred to by the SEQ ID No.) after aligning the sequences and introducing gaps if necessary, to achieve the maximum sequence identity, and not considering any conservative substitutions as part of the sequence identity. Sequence identity is preferably calculated over the entire length of the respective sequences.

Where the aligned sequences are of different length, sequence identity of the shorter comparison sequence may be determined over the entire length of the longer given sequence or, where the comparison sequence is longer than the given sequence, sequence identity of the comparison sequence may be determined over the entire length of the shorter given sequence.

For example, where a given sequence comprises 100 amino acids and the candidate sequence comprises 10 amino acids, the candidate sequence can only have a maximum identity of 10% to the entire length of the given sequence. This is further illustrated in the following example:

```
(A)
Given seq:      XXXXXXXXXXXXXXX  (15 amino acids)
Comparison seq: XXXXXYYYYYYY     (12 amino acids)
```

The given sequence may, for example, be that encoding ING4 (e.g. SEQ ID No.3).

% sequence identity=the number of identically matching amino acid residues after alignment divided by the total number of amino acid residues in the longer given sequence, i.e. (5 divided by 15)× 100=33.3%

Where the comparison sequence is longer than the given sequence, sequence identity may be determined over the entire length of the given sequence. For example:

```
(B)
Given seq:      XXXXXXXXXX  (10 amino acids)
Comparison seq: XXXXXYYYYYYZZYZZZZZ  (20 amino
                                      acids)
```

Again, the given sequence may, for example, be that encoding ING4 (e.g. SEQ ID No.3).

% sequence identity=number of identical amino acids after alignment divided by total number of amino acid residues in the given sequence, i.e. (5 divided by 10)×100=50%.

Alignment for purposes of determining percent amino acid sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

Identity of nucleic acid sequences may be determined in a similar manner involving aligning the sequences and introducing gaps if necessary, to achieve the maximum sequence identity, and calculating sequence identity over the entire length of the respective sequences. Where the aligned sequences are of different length, sequence identity may be determined as described above and illustrated in examples (A) and (B).

Hybridisation Stringency

In accordance with the present invention, nucleic acid sequences may be identified by using hybridization and washing conditions of appropriate stringency.

Complementary nucleic acid sequences will hybridise to one another through Watson-Crick binding interactions. Sequences which are not 100% complementary may also hybridise but the strength of the hybridisation usually decreases with the decrease in complementarity. The strength of hybridisation can therefore be used to distinguish the degree of complementarity of sequences capable of binding to each other.

The "stringency" of a hybridization reaction can be readily determined by a person skilled in the art.

The stringency of a given reaction may depend upon factors such as probe length, washing temperature, and salt concentration. Higher temperatures are generally required for proper annealing of long probes, while shorter probes may be annealed at lower temperatures. The higher the degree of desired complementarity between the probe and hybridisable sequence, the higher the relative temperature which can be used. As a result, it follows that higher relative temperatures would tend to make the reaction conditions more stringent, while lower temperatures less so.

For example, hybridizations may be performed, according to the method of Sambrook et al., ("Molecular Cloning, A Laboratory Manual, Cold Spring Harbor Laboratory Press, 1989) using a hybridization solution comprising: 5×SSC, 5×Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules is to calculate the melting temperature $T_m$ (Sambrook et al., 1989):

$$T_m = 81.5° C. + 16.6 \text{ Log } [Na+] + 0.41(\%G+C) - 0.63(\% \text{ formamide}) - 600/n$$

where n is the number of bases in the oligonucleotide.

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in sequence complementarity.

Hybridisation under high stringency conditions may involve performing the hybridisation at a temperature of Tm-15 or higher. Moderate stringency may be considered to be Tm-25 to Tm-15. Low stringency may be considered to be Tm-35 to Tm-25.

Accordingly, nucleotide sequences can be categorised by an ability to hybridise to a target sequence under different hybridisation and washing stringency conditions which can be selected by using the above equation. The $T_m$ may be used to provide an indicator of the strength of the hybridisation.

The concept of distinguishing sequences based on the stringency of the conditions is well understood by the person skilled in the art and may be readily applied.

Sequences exhibiting 95-100% sequence complementarity may be considered to hybridise under very high stringency conditions, sequences exhibiting 85-95% complementarity may be considered to hybridise under high stringency conditions, sequences exhibiting 70-85% complementarity may be considered to hybridise under intermediate stringency conditions, sequences exhibiting 60-70% complementarity may be considered to hybridise under low stringency conditions and sequences exhibiting 50-60% complementarity may be considered to hybridise under very low stringency conditions.

Nucleic Acids and Polypeptides

In this specification, a nucleic acid encoding an ING4 polypeptide may be any nucleic acid (DNA or RNA) having a nucleotide sequence having a specified degree of sequence identity to SEQ ID NO: 4 or SEQ ID NO: 5, to an RNA transcript of any one of these sequences, to a fragment of any one of the preceding sequences or to the complementary sequence of any one of these sequences or fragments. Alternatively a nucleic acid encoding an ING4 polypeptide may be one that hybridises to one of these sequence under high or very high stringency conditions. The specified degree of sequence identity may be from at least 60% to 100% sequence identity. More preferably, the specified degree of sequence identity may be one of at least 65%, 70%, 75%, 80%, 85%, 86%, 87%, 88%, 89%, 90%, 91%, 92%, 93%, 94%, 95%, 96%, 97%, 98%, 99% or 100% identity.

In this specification, an ING4 polypeptide may be any peptide, polypeptide or protein having an amino acid sequence having a specified degree of sequence identity to SEQ ID NO: 3 or to a fragment of one of these sequences. The specified degree of sequence identity may be from at least 60% to 100% sequence identity. More preferably, the specified degree of sequence identity may be one of at least 65%, 70%, 75%, 80%, 85%, 86%, 87%, 88%, 89%, 90%, 91%, 92%, 93%, 94%, 95%, 96%, 97%, 98%, 99% or 100% identity.

Administration

The HSV for use in the present invention may be formulated as medicaments and pharmaceutical compositions for clinical use and may comprise a pharmaceutically acceptable carrier, diluent or adjuvant. The composition may be formulated for topical, parenteral, systemic, intravenous, intra-arterial, intramuscular, intrathecal, intraocular, intratumoural, subcutaneous, oral or transdermal routes of administration which may include injection. Injectable formulations may comprise the selected compound in a sterile or isotonic medium. Medicaments and pharmaceutical compositions may be formulated in fluid or solid (e.g. tablet) form. Fluid formulations may be formulated for administration by injection to a selected region of the human or animal body.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

HSV capable of targeting cells and tissues are described in (PCT/GB2003/000603; WO 03/068809), hereby incorporated in its entirety by reference.

A composition may be administered alone or in combination with other treatments, either simultaneously or sequentially dependent upon the condition to be treated.

The invention includes the combination of the aspects and preferred features described except where such a combination is clearly impermissible or expressly avoided.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which.

Survival data from groups of six mice bearing CP70 subcutaneous tumour implants following intratumoral injections on days 1 and 3 of PBS, HSV1790 or HSV1716ING4. HSV1716 expressing ING4 improves tumour kill in mice with subcutaneous ovarian tumour implants compared to HSV1716 alone. Reduced expression of ING4 is associated with glioma progression. ING4 prevents new growth by inhibition of angiogenesis.

FIG. 4.

Tumour growth data from groups of six mice bearing A431 subcutaneous tumour implants following intratumoral injections on days 1 and 3 of PBS, HSV1716 or HSV1716ING4. HSV1716 expressing ING4 reduces tumour burden in mice with subcutaneous SCC tumour implants compared to HSV1716 alone.

FIG. 5.

Survival data from groups of six mice bearing A431 subcutaneous tumour implants following intratumoral injections on days 1 and 3 of PBS, HSV1716 or HSV1716ING4. HSV1716 expressing ING4 improves tumour kill in mice with subcutaneous SCC tumour implants compared to HSV1716 alone.

FIG. 6.

Median survival. HSV1716 expressing ING4 extends survival times in mice with subcutaneous SCC tumour implants compared to HSV1716 alone.

FIG. 7.

Tumour growth data from groups of ten mice bearing A431 subcutaneous tumour implants following intravenous injections on days 1 and 3 of PBS, $1\times10^6$ pfu HSV1716 or $1\times10^6$ pfu HSV1716ING4.

DETAILED DESCRIPTION OF THE INVENTION

Specific details of the best mode contemplated by the inventors for carrying out the invention are set forth below, by way of example. It will be apparent to one skilled in the art that the present invention may be practiced without limitation to these specific details.

An HSV1716 Variant Expressing the Tumour Suppressor Gene Inhibitor of New Growth 4

Methods and Results

Figure 1:
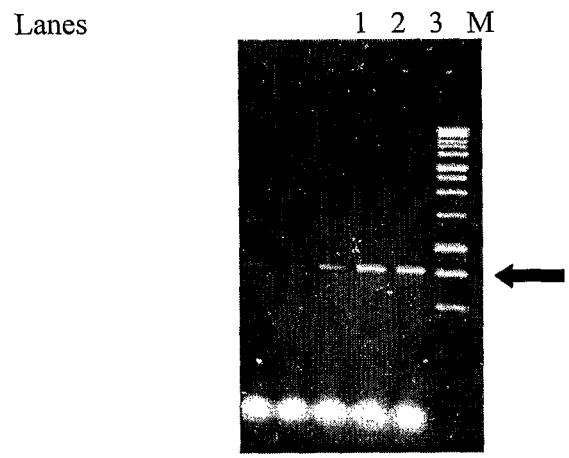
FIG. 1 shows a 1% agarose/TAE gel showing PCR products amplified from either liver (lane 1) or placental (lanes 2 and 3) cDNA libraries. The c750 bp ING4 cDNA is arrowed. Lane M=2-log DNA ladder.

An HSV1716 variant expressing the ING4 tumour suppressor gene was constructed as follows. Primers for the PCT amplification of ING4 were designed using the human ING4 sequence deposited in the NCBI at ncbi.nlm.nih.gov under Accession No. NM_016162 GI:38201669). The forward primer GA<u>GAATTCGCGGCCGCG</u>ATGGCTGCGGGGATGTATTTG (SEQ ID No.1) hybridises at the ATG start codon of ING4 (in bold) and incorporates EcoR1 and Not1 restriction sites (underlined) upstream of the translation start site. The reverse primer AG<u>TCTAGACTCGAG</u>CTATTTCTTCTTCCGTTCTTGGGA (SEQ ID No.2) hybridises 36 nucleotides downstream (ING4 sequence in bold) from the TAG stop codon of ING4 and incorporates Xho1 and Xba1 sites (underlined). The c750 bp cDNA encoding ING4 (SEQ ID No.5) was successfully amplified from commercially available human liver and placental cDNA libraries (FIG. 1) and, as a stronger band was obtained with the placental cDNA (lanes 2 and 3) library, this was used for ING4 cloning.

The PCR product was ligated into the pGEM-Teasy vector and sequencing confirmed a 100% match with NM016162. The PCR product was then digested directly with EcoR1 followed by Xba1 and ligated into the likewise digested mammalian expression vector pCDNA4-myc-His (Invitrogen, Paisley, UK). Positive clones were identified by BamHI digestion of miniprepped DNA (there is an internal ING4 BamHI site at nucleotide 608) and the ING4 expression cassette (CMV-IE promoter from plasmid plus ING4 cDNA) was excised from a positive clone by NruI/XhoI digestion, blunt ended using Klenow and cloned into the BglII digested, blunt ended and CIAP treated RL1 shuttle vector pRL1del/gfp used for the production of HSV1716 variants by homologous recombination. RL1del/gfp is a modified version of pRL1-del containing an expression cassette for gfp (PGK-gfp). RL1-del is a promoterless cloning vector, suitable for generating ICP34.5 null HSV-1. It contains a HSV-1 fragment formerly consisting of the RL1 gene and its flanking sequences with the majority of the RL1 gene removed and replaced with a multi-cloning sequence (MCS). The transgene to be inserted into the RL1 loci is ligated into the MCS of RL1-del and homologous recombination with HSV-1 DNA, driven by the RL1 flanking sequences, results in concomitant deletion of the ICP34.5 open reading frame and incorporation of the appropriate transgene. To assist in plaque purification of recombinant viruses, the green fluorescent protein gene is also inserted into the MCS of RL1-del.

RL1-del contains the HSV-1 BamHI k DNA fragment 123459-129403 which includes the RL1 gene and its flanking sequences cloned into the BamHI site of plasmid pGem-3Zf (Promega, Southampton, UK). The 477 bp PflMI/BstEII fragment from the RL1 ORF (125292-125769) has been removed to inactivate the ICP34.5 gene and replaced with a MCS providing various restriction enzymes sites including those for BglII, NruI and XhoI.

RL1-del is described in WO2005/049844.

To create RL1-del/gfp, the 1.3 kbp blunt-ended EcoRI/AflII fragment that contains the PGK promoter/gfp gene was obtained by restriction digestion followed by Klenow treatment from the vector pSNRG (OligoEngine, Seattle, Wash., USA) and ligated into the RL1-del vector cut with the restriction enzyme NruI then alkaline phosphatase treated.

Figure 2:
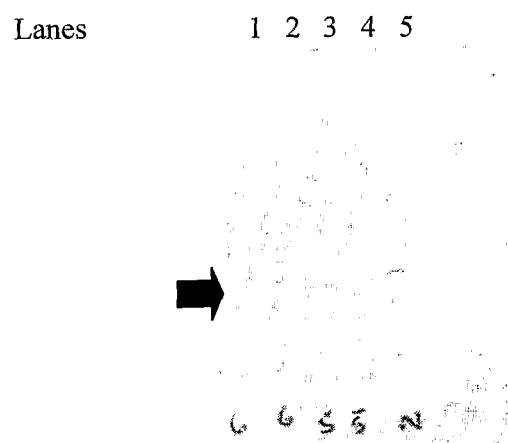
FIG. 2 shows a Western blot probed with an anti-ING4 antibody at 1:500. The arrow indicates the position in lanes 1 and 2 of the 29 kDA ING4 protein present in whole cell extracts from BHK cells infected with 1 pfu/cell HSV1716ING4. This band is also faintly visible in cells infected with 0.1 pfu/cell HSV1716ING4 (lanes 3 and 4) but is absent from mock infected cells (lane 5).

Insertion of the ING4 expression cassette in pRL1-del/gfp was confirmed by restriction enzyme digests and 50 μg of plasmid were linearized by ScaI digestion and, after column clean-up using a GFX kit (GE Healthcare, Little Chalfont, UK), were used in conjunction with HSV-1 DNA to cotransfect BHK cells. RL1-del/gfp/ING4 and viral DNA (c100 ug) were mixed with 20 μl lipofectamine 2000 in 250 μl DMEM/F12 serum-free medium and added to a 60 mm plate which contained 50% confluent BHK cells. After 4 hours of incubation at 37° C. the medium was removed and the cells shocked for exactly 4 minutes with 25% DMSO. After 3 washes with 5 ml culture medium the cells were returned to 37° C. with 5 ml BHK medium and left for 72 hours. Cells were then scraped into the supernatant, the mixture sonicated in a sonicator bath for 2 minutes and stored at −70° C. until required. Serial dilutions were then plated out on Vero cells in 60 mm dishes, individual green fluorescent plaques were picked, added to 1 ml culture medium and sonicated in a sonicator bath for 2 minutes before serial dilutions were again plated out on Vero cells. Plaque purification was repeated 6 times before stocks of HSV1716ING4 were produced. The presence of the ING4 expression cassettes in the RL1 loci of HSV1716 was confirmed by both Southern blotting using the AluI/RsaI ICP34.5 fragment from plasmid pGEM34.5 and by PCR using primers which amplify across the ICP34.5 deleted region of HSV1716. To confirm expression of the inserted ING4 transgene confluent monolayers of BHK cells in 60 mm plates were infected with either 0.1 or 1 pfu/cell HSV1716ING4 and, after 24 hours, whole cells extracts were prepared by the addition of 0.2 ml SDS PAGE sample buffer. SDS PAGE/Western blotting using an ING4 antibody (Abcam, Cambridge, UK) identified a c29 kDa protein in the cells infected with 1 pfu/cell HSV1716ING 4 (FIG. 2, lanes 1 and 2). A weaker band was observed in the cells infected with 0.1 pfu/cell HSV1716ING4 (FIG. 2; lanes 3 and 4) and this protein was absent from mock infected cells (FIG. 2, lane 5).

Example 1

In Vivo Experiments

Intratumoral Injection of Nude Mice Bearing Subcutaneous Tumour Implants

Figure 3:
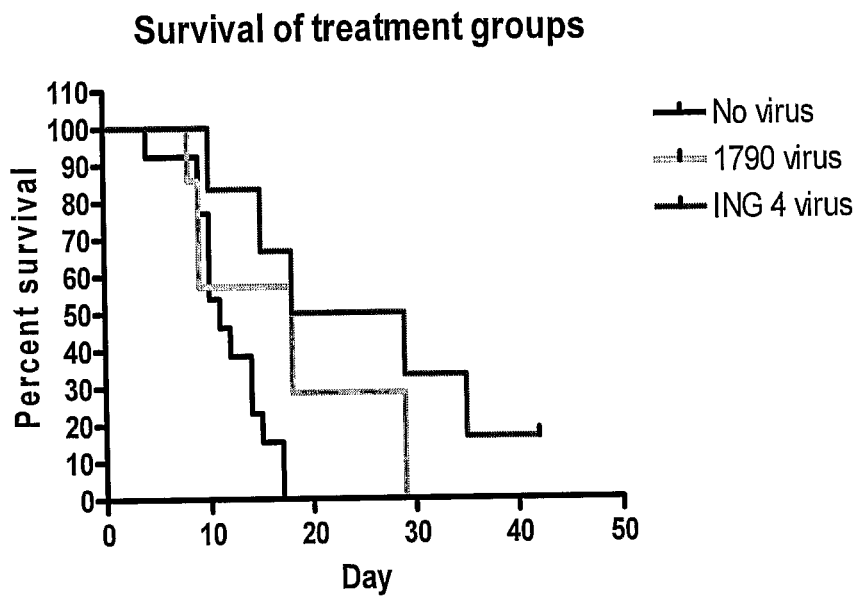
FIG. 3.

In an initial experiment, 6 mice with subcutaneous implants of the CP70 ovarian tumour cell line were injected intratumorally with $1 \times 10^7$ pfu HSV1716ING4 on days 1 and 3 and tumour growth and survival was monitored daily. Control mice were either injected with HSV1790, an HSV1716 variant expressing the enzyme nitroreductase, or were injected with a similar volume of PBS. Survival data is shown in FIG. 3.

Of the 6 mice treated with HSV1716ING4, 1 tumour showed complete regression, 4 tumours grew at a slower rate than the untreated tumours and 1 tumour became ulcerated and the mouse was removed from the analysis. Using survival times (as measured by when the tumour reached the upper acceptable limit) to assess each of the treatments, animals treated with the ING 4 virus had an average survival of 23.5 days compared to animals treated with no virus or those treated with HSV1790 which had survival times of 11 or 18 days respectively. Log rank comparison of the survival curves shown in FIG. 3 demonstrated significant differences with a p value of 0.03. Note that no CB1954 was administered to mice infected with HSV1790 and, under these circumstances this virus is equivalent to HSV1716.

In a subsequent experiment, groups of 6 mice bearing subcutaneous implants of human SCC A431 tumour cells were given injections on Days 1 and 3 of either $1 \times 10^7$ pfu HSV1716ING4 or HSV1716 or an equivalent volume of PBS and tumour growth and survival were determined daily.

Figure 4:
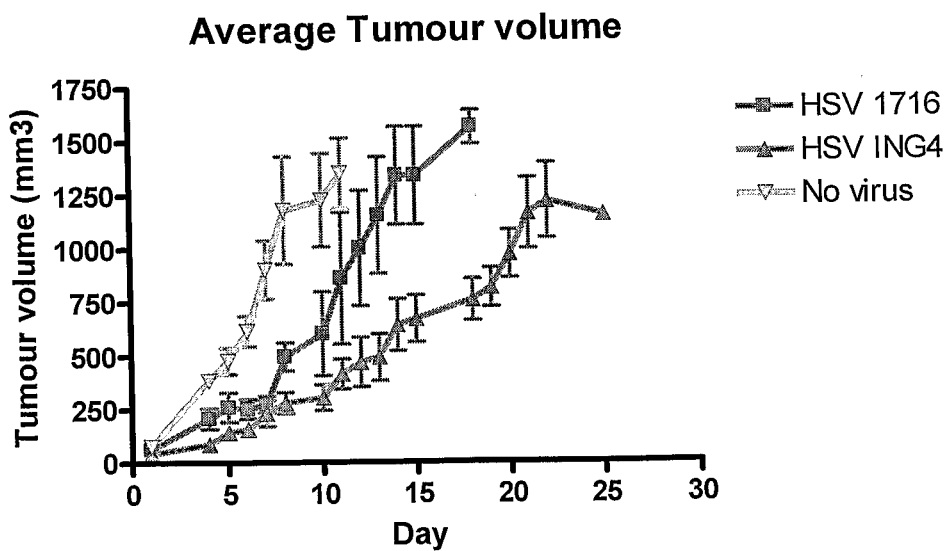

FIG. 4 shows the average tumour volumes and demonstrated that the group treated with HSV1716ING 4 had a smaller average tumour volume than either the group treated with no virus or with the parental HSV1716. Statistical analysis showed that the differences in tumour volumes between HSV1716ING4 and HSV1716 and between HSV1716ING4 and no virus at day 15 were significantly different with P=0.03 and P=0.007 respectively.

Figure 5:
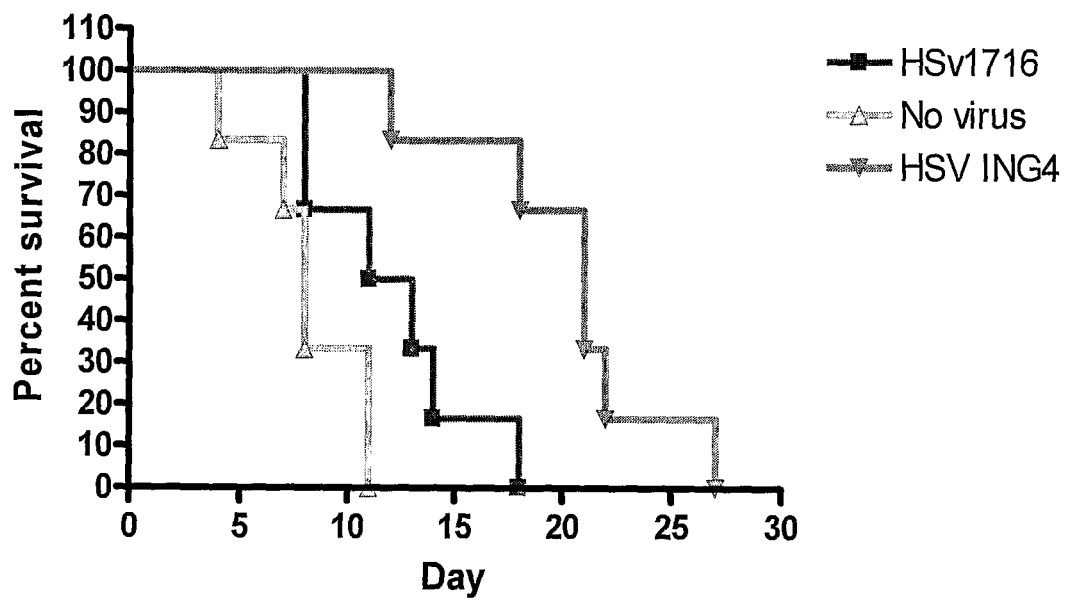

FIG. 5 shows the KM survival graph for the tumour-bearing mice treated with no virus, HSV1716 or HSV1716ING 4. Mice treated with no virus had a median survival of 8 days, those treated with HSV1716 had a median survival of 12 days and those treated with HSV1716ING 4 had a median survival of 21 days. Comparison of the FIG. 5 curves by log rank analysis shows that the difference between them is significant with p=0.004 thus clearly demonstrating in this tumour model that HSV1716ING4 significantly reduced tumour burdens and enhanced survival.

Intravenous Injection

Figure 6:
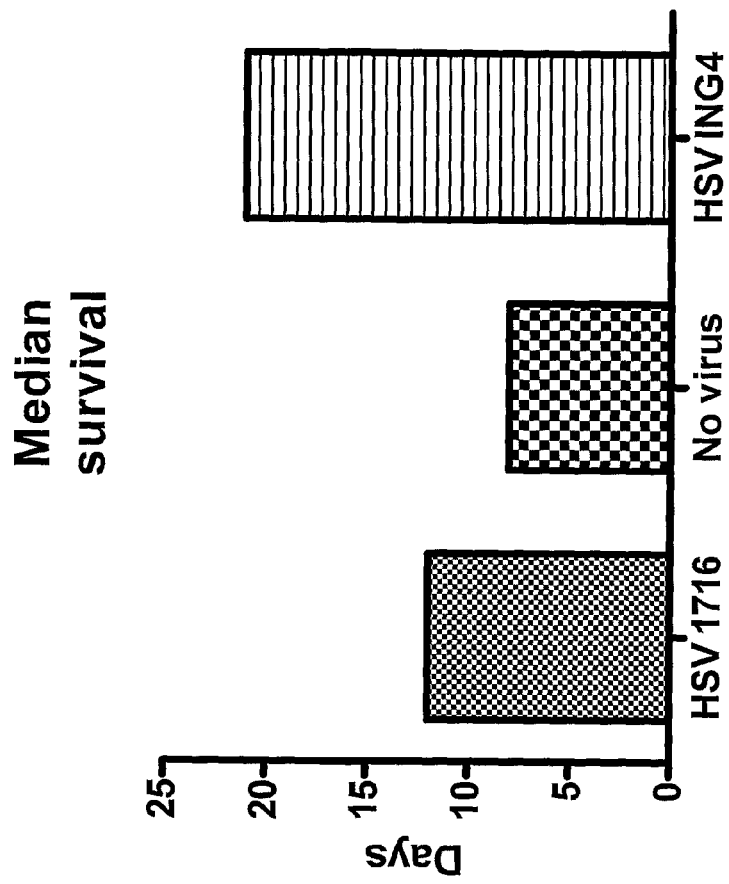
Figure 7:
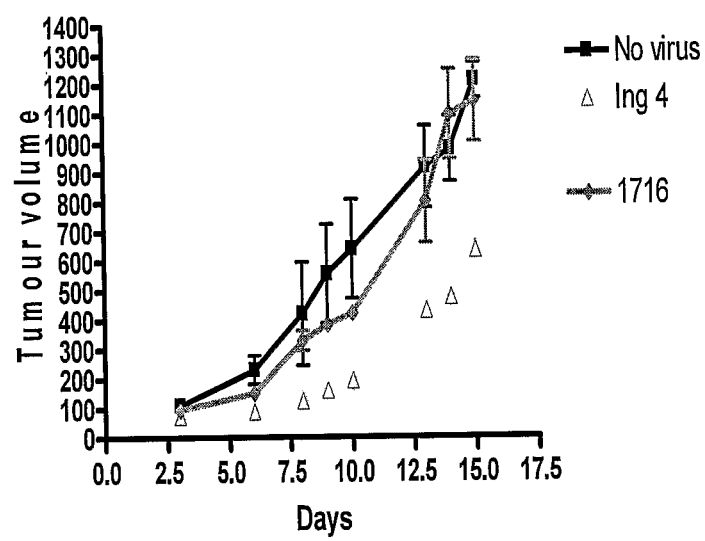

Groups of 10 mice with subcutaneous human SCC A431 tumours were intravenously injected with PBS (no virus) or with $1 \times 10^6$ pfu HSV1716 or HSV1716ING4 on days 1 and 3 and tumour growth and survival was monitored daily. After intravenous injection HSV1716ING4 significantly reduced tumour growth compared to no virus controls or to unmodified HSV1716 (FIG. 6). On day 10 post injection, the mean tumour volume for HSV1716-injected mice was 421±55 mm$^2$ compared to 193±152 mm$^2$ for HSV1716ING4 injected mice and, using Student's t test, this difference is highly significant with p=0.0022. Similarly, on days 14 or 20, the average tumour volumes for HSV1716-injected mice were 1096±402 mm$^2$ or 1253±155 mm$^2$ respectively versus 476±448 mm$^2$ or 776±438 mm$^2$ respectively for mice receiving HSV1716ING4 and, using Student's t test, both these differences are significant with p=0.0125 or 0.0162 respectively. Mice receiving no virus or $1 \times 10^6$ pfu HSV1716 had median survivals of approximately 14 days, whereas mice receiving HSV1716ING4 had a median survival of 17 days with 4/10 mice surviving beyond day 20 by which time all the PBS- or HSV1716-injected mice had been sacrificed. A number of tumours from each of the groups of mice were removed at sacrifice and, after mechanical homogenisation, virus in the tumour extract was titrated with the results presented in Table 1.

Virus was readily extracted from all three tumours taken from the mice which received intravenous HSV1716ING4 but was only detected in ⅓ mice which received HSV1716 and the amounts of virus detected in the HSV1716ING4 tumours were approximately 1000-fold greater than the amount extracted from the HSV1716 tumour suggesting better replication of HSV1716ING4 than HSV1716 within the tumour. Previous studies, albeit in immunocompetent rats, have shown that only 0.001% of intravenously injected virus lodges in the tumour 24 hours after administration (Schellingerhout et al 1998, 2000) and, assuming that this provides a reasonable approximation for SCID mice, then, of the $2 \times 10^6$ pfu administered intravenously, only 20 pfu will reach the tumour initially. Assuming that there is no difference in biodistribution between HSV1716 and HSV1716ING4, the above data demonstrates that HSV1716ING4 is significantly better at replication within human A431 SCC tumour implants than HSV1716 and that this enhanced propagation improves survival. One of the HSV1716ING4 mice survived until day 30, by which time the tumour had stopped growing and was almost completely regressed. After sacrifice of this mouse, all its organs were harvested including residual tumour tissue and, following mechanical homogenisation and titration, no virus was found in any of these tissues suggesting complete recovery and viral clearance in this mouse. Indeed, there was no evidence of viral toxicity in any of the mice which received HSV1716ING4 indicating that the virus retains the restricted replication competence of the parental HSV1716 with propagation limited to the actively dividing tumour cells.

Example 2

In Vitro Experiments

Propagation of HSV1716ING4 on Different Cell Lines

The above in vivo data suggests that HSV1716ING4 demonstrates enhanced oncolysis by replicating with higher efficiency than unmodified HSV1716 and this was confirmed in vitro using a variety of different cells lines infected at low multiplicities of infection. Cell lines used were BHK, Vero, A431 human SCC, CP70 human ovarian tumour, MDA-MB-468 human breast adenocarcinoma, Ovcar3 human ovarian carcinoma and HuH7 human hepatocellular carcinoma and propagation of HSV1716ING4 in these lines was compared with wild-type HSV-1 17+, HSV1716, HSV1716ING4 and HSV1716EGFR (an EGFR-targeted HSV1716 variant that expresses a targeting moiety approximately the same molecular size as ING4).

Cells were plated out in 60 mm dishes and after 24 hours they were infected with approximately 100 pfu (BHK only) or 1000 pfu (all other cell types) HSV-1 17+, HSV1716, HSV1716ING4 or HSV1716EGFR. Dilutions of each virus preparation for these infections were titrated on BHK cells to confirm accurately the amounts of input virus. Each virus infection on each cell type was performed in quadruplicate at least. After 72 hours of infection, cells and medium were harvested, subjected to one freeze/thaw cycle (−70° C.) and titrated on BHK cells. The results in the Tables 2-8 below are reported in yields/input virion with statistical comparisons made using ANOVA.

For BHK cells, the high yields of virus/input virion for HSV-1 17+, HSV1716 and HSV1716ING4 are very similar indicating that these three viruses have similar replication efficiencies in this cell type and the yields, equivalent to approximately $5 \times 10^6$ viruses per input virion, are probably the maximum output achievable from a 100 pfu infection of BHK cells in this experiment. For HSV1716EGFR yields/input virus were approximately 10-fold less than for HSV-1 17+, HSV1716 and HSV1716ING4 suggesting that, in this experiment, this virus replicates less efficiently in BHK cells, see Table 2.

In Vero cells, HSV1716ING4 replicates more efficiently than HSV-1 17+, HSV1716 or HSV1716EGFR with at least a 2-fold increase in yield/input virion, see Table 3. Comparisons of the yield/input virion for HSV1716ING4 with each of the yields/input virion for HSV-1 17+, HSV1716 or HSV1716EGFR indicated that these differences are significant. ANOVA analysis of the data in Table 3 gives significant p values of p<0.01, p<0.05 or p<0.001 respectively for HSV1716ING4 compared to HSV-1 17+, HSV1716 or HSV1716EGFR and, since all of these values are above the 95% confidence limit, it can be concluded that the presence of the ING4 expression cassette in HSV1716ING4 improves virus replication in this cell type.

In a separate experiment, $5 \times 10^5$ Vero cells were plated out in 60 mm dish and were allowed to attach for 6 hours before being infected in duplicate at a multiplicity of infection of 1 pfu/cell with HSV-1 17+, HSV1716, HSV1716ING4 or HSV1716EGFR. After exactly 24 hours in culture, cells and medium were harvested, subjected to one freeze/thaw cycle (−70° C.) and titrated on BHK cells. For HSV1716ING4, the yields of virus/infected cell were approximately twice the yields of virus/infected cell for HSV-1 17+, HSV1716 or HSV1716EGFR. At an input of 1 pfu/cell, HSV1716ING4 produced 140/250 virions/infected cell compared to 50/70 for HSV-1 17+, 80/88 for HSV1716 or 50/70 for HSV1716EGFR. Thus, during 24 hours of infection in Vero cells (equivalent to one round of virus replication), HSV1716ING4 must replicate more efficiently than HSV-1 17+, HSV1716 or HSV1716EGFR.

For the human ovarian cancer cell line Ovcar 3 cells, HSV1716ING4 replicates more efficiently than HSV-1 17+, HSV1716 or HSV1716EGFR with a 2-4-fold increase in yield/input virion, see Table 4. Comparing the yield/input virion for HSV1716ING4 with each of the yields/input virion for HSV-1 17+, HSV1716 or HSV1716EGFR indicates that the differences are significant. ANOVA analysis of the data in Table 4 gives p values all of p<0.001 for HSV1716ING4 compared to each of HSV-1 17+, HSV1716 or HSV1716EGFR and, since all of these are highly significant with greater than 99.9% confidence limits, HSV1716ING4 must replicate more efficiently in this cell type.

For the human squamous cell carcinoma cell line A431, HSV1716ING4 replicates more efficiently than either HSV1716 or HSV1716EGFR with a 100-fold increase in yield/input virion compared to HSV1716 and 10-fold increase compared to HSV1716EGFR, see Table 5. Statistical comparison of the yield/input virion for HSV1716ING4 with the yields/input virion for either HSV1716 or HSV1716EGFR by ANOVA gives p values of p<0.05 for both indicating that the differences are significant with the greater than 95% confidence limit indicating that, compared to the parental HSV1716 or the HSV1716 variant HSV1716EGFR, HSV1716ING4 must replicate more efficiently in this cell type. The mean yield/input virion for HSV1716ING4 is greater than the mean yield/input virion for wild type HSV-1 17+ but the difference is not significant (p>0.05). However, although HSV-1 17+ has a higher mean yield/input virion than either HSV1716 of HSV1716EGFR, neither of these differences is significant (both p>0.05). Similarly, although the mean yield/input virion for HSV1716EGFR is higher than the mean yield/input virion for HSV1716, the difference is not significant (p>0.05). When the yields/input virion for HSV1716ING4 and HSV-1 17+ are compared using the less stringent Student's t test, the differences are significant with p=0.004 suggesting that HSV1716ING4 replicates more efficiently in A431 cells than HSV-1 17+.

In the human breast adenocarcinoma cells, HSV1716ING4 replicates more efficiently than HSV-1 17+, HSV1716 or HSV1716EGFR with an approximately 10-fold increase in yield/input virion, see Table 6. For HSV1716ING4, comparison of the yield/input virion with each of the yields/input virion for HSV-1 17+, HSV1716 or HSV1716EGFR indicates that the differences are significant. ANOVA analysis of the data in Table 6, gives significant p values, all of p<0.001, for HSV1716ING4 compared to each of HSV-1 17+, HSV1716 or HSV1716EGFR and these are highly significant with greater than 99.9% confidence limits indicating that HSV1716ING4 replicates more efficiently in this cell line.

For the human ovarian cancer cell line CP70, HSV1716ING4 replicates more efficiently than either HSV1716 or HSV1716EGFR with a 3-fold increase in yield/input virion compared to HSV1716 or HSV1716EGFR, see Table 7. Statistical comparison of the yield/input virion for HSV1716ING4 with the yields/input virion for either HSV1716 or HSV1716EGFR by ANOVA gives p values of p<0.01 for both indicating that the differences are significant with the greater than 99% confidence limit indicating that, compared to the parental HSV1716 or the HSV1716 variant HSV1716EGFR, HSV1716ING4 must replicate more efficiently in this cell type. There was no significant difference between the yields/input virion for HSV1716 and HSV1716EGFR (p>0.05). The mean yield/input virion for HSV1716ING4 was not significantly different from the mean yield/input virion for wild type HSV-1 17+ (p>0.05). However, HSV-1 17+ replicated more efficiently than either HSV1716 or HSV1716EGFR and these differences were significant (p<0.01) indicating that HSV1716/HSV1716EGFR are impaired for replication in this cell type. Importantly, expression of ING4 overcomes this impairment and returns the efficiency of replication to wild-type levels.

In the human HuH7 hepatocellular carcinoma cells, HSV1716ING4 replicates more efficiently than HSV-1 17+, HSV1716 or HSV1716EGFR with an approximately 5-fold increase in yield/input virion, see Table 8. For HSV1716ING4, comparison of the yield/input virion with each of the yields/input virion for HSV-1 17+, HSV1716 or HSV1716EGFR indicated that the differences are significant. ANOVA analysis of the data in Table 8 gives significant p values, all of p<0.001, for HSV1716ING4 compared to each of HSV-1 17+, HSV1716 or HSV1716EGFR and, as these are highly significant with greater than 99.9% confidence limits, HSV1716ING4 must replicate more efficiently in this cell line.

A hallmark of the attenuated HSV1716 phenotype in vitro is the inability of the virus to replicate in NIH 3T6 cells whereas these cells are fully permissive for HSV-1 17+ replication. In duplicate, NIH 3T6 cells in 60 mm plates were infected with 1000 pfu HSV-1 17+, HSV1716, HSV1716ING4 and HSV1716EGFR. After 72 hours of infection, cells and medium were harvested, subjected to one freeze/thaw cycle (−70° C.) and titrated on BHK cells. No virus was detected following infection of 3T6 cells with HSV1716, HSV1716ING4 or HSV1716EGFR whereas the yields from duplicate HSV-1 17+ infections of 3T6 cells were $2.0 \times 10^6 / 3.0 \times 10^6$ pfu. Therefore, the ability of ING4 expression to enhance the replication of HSV1716 is not achieved at the expense of its attenuated phenotype and ING4 activity within the infected cell is unable to overcome the replicative restrictions caused by deletion of the ICP34.5 gene.

Propagation on BHK Cells Engineered to Constitutively Express ING4

To generate HSV1716ING4, the ING4 cDNA was initially cloned into the mammalian expression plasmid pCDNA4/myc-HisA and this vector was used to create BHK cell lines which constitutively express ING4. BHK cells were transfected with 100 ug of the ING4 expression vector or with the empty pCDNA4/myc-HisA plasmid mixed with 10 ul lipofectamine 2000 (Invitrogen) in 250 ul of serum free DMEM/F12 medium. After 72 hours of transfection, cells were trypsinized and plated out with growth medium containing 1 mg/ml zeocin (Invitrogen). Cells were selected with the zeocin antibiotic for 2-3 weeks after which time individual clones were clearly visible. Cells were trysinized and cloned by limiting dilutions in 24-well plates. Five clones of BHK/ING4 or BHK/pCDNA4 were expanded and maintained in appropriate medium containing 0.5 mg/ml zeocin.

Each of the clones was plated out in 60 mm dishes in medium without zeocin and after 24 hours they were infected with approximately 10 pfu HSV-1 17+ or HSV1716. After 72 hours of infection, cells and medium were harvested, subjected to one freeze/thaw cycle (−70° C.) and titrated on BHK cells. Dilutions of each virus prepared for the infections were also titrated to confirm accurately the amounts of input virus and the results in the Tables 9 and 10 below are reported in yields/input virion with statistical comparisons made using Student's T test.

Propagation of HSV-1 17+ on BHK cells engineered by transfection/antibiotic selection to express constitutively ING4 is approximately 10-fold more efficient when compared with propagation on zeocin-resistant BHK cells produced using the empty pCDNA4.myc-His vector. Comparison of the means using Student's t test indicates that this difference is highly significant with p<0.0001 indicating a greater than 99.99% confidence limit that ING4 expression improves HSV-1 17+ replication in BHK cells.

Propagation of HSV1716 on BHK cells engineered by transfection/antibiotic selection to express constitutively ING4 is approximately 10-fold more efficient when compared with propagation on zeocin resistant BHK cells generated by transfection with the empty pCDNA4.myc-His vector. Comparison of the means using Student's t test demonstrates that this difference is highly significant with p=0.02 indicating a confidence limit of 98% that ING4 expression improves HSV1716 replication in BHK cells.

Example 3

Preliminary In Vitro Experiments

The in vivo data suggested that HSV1716ING4 replicated with higher efficiency than unmodified HSV1716. This was initially confirmed in vitro using a variety of different cells lines infected at low multiplicities of infection, as described below. These experiments were followed up with the experiments described in Example 2.

Cell lines used were BHK, Vero, 3T6, A431 human SCC, CP70 ovarian tumour, MDA human breast carcinoma, Ovcar3 human ovarian carcinoma and UVW human glioblastoma and they were infected principally with HSV1716, HSV1716ING4 and HSV1716EGFR.

Experiment 1. Cells were plated out in 60 mm dishes and after 24 hours they were infected with 1, 10 or 100 pfu HSV1716, HSV1716ING4 or HSV1716EGFR. After 72 hours of infection, cells and medium were harvested, subjected to one freeze/thaw cycle (−70° C.) and, as each of these viruses expresses gfp, a TCID method was used to estimate the amounts of virus in each sample. Results are presented in Tables 11-14 below.

Experiment 1 clearly demonstrates that in all cell types except 3T6 cells, HSV1716ING4 replicates more efficiently than HSV1716 resulting in higher yields of virus at inputs of 1, 10 and 100 pfu. All three viruses used failed to replicate in 3T6 cells confirming their HSV1716 phenotype.

Experiment 2. Cells were plated out in 60 mm dishes and after 24 hours they were infected in duplicate with 5 or 20 pfu HSV1716, HSV1716ING4 or HSV1716EGFR. After 72 hours of infection, cells and medium were harvested, subjected to one freeze/thaw cycle (−70° C.) and, as each of these viruses expresses gfp, a TCID method was used to estimate the amounts of virus in each sample. Results are presented in Tables 15-17 below.

Again, experiment 2 clearly demonstrates that in all cell types HSV1716ING4 replicates more efficiently than HSV1716 resulting in higher yields of progeny virus at inputs of 5 or 20 pfu. The enhancement to HSV1716ING4 propagation is more pronounced at 5 pfu virus especially in Ovcar3 and A431 cells in which HSV1716ING4 yields are up to 100-fold greater than HSV1716.

Experiment 3. Each of the above cell types was seeded in a T175 flask and once confluent, the cells were infected with HSV-1 17+, HSV1716, HSV1716ING4 or HSV1716EGFR. After 96 hours in culture, virus was harvested from both detached cells and supernatant by high speed centrifugation and titrated on BHK cells. The dilutions used to infect the flasks were also titred on BHK cells to quantitate accurately the amount of input virus. For each cell type, total amounts of virus/flask, % yields from input and the % yield ratios compared to the HSV1716% yield ratio are presented in Table 18.

CONCLUSIONS

An HSV1716 variant expressing the candidate tumour suppressor gene ING4 shows significantly enhanced inhibition of tumour growth and prolonged survival times when compared with HSV1716 alone. Indeed, although not compared directly in the above experiments, the survival times for CP70 tumour-bearing mice treated with HSV1716ING4 were similar to those obtained following treatment with the nitroreductase-expressing variant HSV1790 in conjunction with the prodrug CB1954. The enhanced survival times in the two models is unexpected and surprising given the postulated activities of ING4 as a subunit of various complexes involved in regulating transcription as such a mode of action in the infected tumour cells would not be expected to have such a dramatic effect on cytotoxicity against the background of an HSV1716 lytic infection. Thus, the virus itself efficiently kills dividing tumour cells more rapidly than any toxic effects resulting from ING4 overexpression. Possibly, ING4 expression destroys tumour cells which are infected but are resistant to virus oncolysis but this seems unlikely as the proportion of these cells in any given tumour will not be sufficient to account for the enhanced tumour destruction seen with HSV1716ING4.

Alternatively, ING4 expressed in the infected tumour cell results in the release of anti-angiogenesis agents such as IL-6 or IL-8 which may act locally on surrounding uninfected cells within the tumour to suppress angiogenesis leading to enhanced tumour destruction. Thus, according to this hypothesis, ING4 expression will stimulate release of locally-acting messengers from the infected cell which will act upon adjacent uninfected cells resulting in suppressed expression of genes promoting angiogenesis leading to a reduction in tumour vascularization and enhanced tumour destruction.

Moreover, mice which received intratumoral injections of PBS into either CP70 human ovarian cancer cell or A431 SCC implants had median survivals of 11 or 8 days respectively. Oncolytic infection of tumour cells by HSV1716 extended median survival in both theses models to 18 or 12 days respectively. Further extensions to survival times to 23.5 or 21 days occurred with HSV1716ING4 injections indicating that the ING4 expression significantly augments HSV1716 oncolytic potency. Intravenous injection of HSV1716ING4 also reduced tumour growth and prolonged survival compared to intravenously injected HSV1716 and extraction and titration of virus from the tumour implants of sacrificed mice indicated a potential mode of action for the enhance tumour cell killing by HSV1716ING4. At least 1000-fold more viruses were extracted from tumours of mice intravenously injected with HSV1716ING4 compared to mice treated with unmodified HSV1716 suggesting that the expression of ING4 in the HSV1716-infected cell improves the efficiency of virus replication resulting in augmented progeny production. Thus, during HSV1716ING4 infection, the ING4 protein conditions the cell such that it provides an improved environment for HSV1716 replication. Consequentially, more progeny virions are produced per tumour cell infected and this enhancement to oncolysis reduces tumour cell numbers and promotes survival. Experiments in vitro with a panel of different cell lines confirmed that ING4 expression improves the efficiency of HSV1716 replication in a panel of different human tumour cell lines.

BHK cells are routinely used for the growth of wild type HSV-1 17+ and HSV1716 and its variants as the cell line is an excellent substrate for viral replication and high yields are always obtained. For HSV-1 17+, HSV1716 and HSV1716ING4 approximately $5\times10^8$-$1\times10^9$ pfu were obtained by infecting a 60 mm plate with c100 pfu virus and there was little difference in the yields/input virion probably because this is the maximum output for BHK cells in this culture format. Vero cells can also be used for HSV-1 propagation although in this experiment the yields/input virion for HSV-1 17+, HSV1716, HSV1716ING4 and HSV1716EGFR were lower than for BHK cells. At low moi, HSV1716ING4 replicated with a 2-fold higher efficiency in Vero cells compared to HSV-1 17+, HSV1716 or HSV1716EGFR and statistical comparison, using the stringent ANOVA test, of HSV1716ING4 with each of these other viruses indicated that the differences were significant. No significant differences were detected in yields/input virion amongst HSV-1 17+, HSV1716 and HSV1716EGFR. Further, using a much higher moi of 1 pfu/cell to infect Vero cells for one lytic cycle, HSV1716ING4 again replicated with twice the efficiency compared to HSV-1 17+, HSV1716 or HSV1716EGFR indicating that the growth advantage conferred by ING4 expression occurs within a single lytic cycle.

In preliminary in vitro experiments with a panel of human tumour cell lines (CP70 human ovarian tumour, MDA-MB-468 human breast adenocarcinoma, Ovcar3 human ovarian carcinoma, UVW human glioblastoma and A431 SCC cells), HSV1716ING4 demonstrated enhanced replication in each of these cell types compared to either HSV1716 or HSV1716EGFR. In subsequent experiments using numbers of replicates that allowed for statistically meaningful comparisons, significantly increased yields/input virion for HSV1716ING4 compared to yields/input virion for HSV1716 or HSV1716EGFR were obtained in CP70 human ovarian tumour, MDA-MB-468 human breast adenocarcinoma, Ovcar3 human ovarian carcinoma, HuH7 human hepatocellular carcinoma and A431 SCC cells with the HSV1716ING4 output enhanced by 2-fold, 10-fold, 5-fold, 5-fold and 10-100-fold respectively in these cell types. Significant differences were also obtained between HSV1716ING4 and HSV-1 17+ replication in MDA-MB-468 human breast adenocarcinoma, Ovcar3 human ovarian carcinoma and HuH7 human hepatocellular carcinoma cells but there was no difference in replication efficiency between these two viruses in CP70 human ovarian tumour cells. For A431 SCC cells, HSV1716ING4 output was significantly increased by 100-fold or 10-fold compared to HSV1716 or HSV1716EGFR respectively and, although using ANOVA, the 2-fold higher HSV1716ING4 yield/input virion was not significantly different from that of HSV-1 17+, the difference was significant when the means were compared using Student's t test. As with the MDA-MB-468 human breast adenocarcinoma, Ovcar3 human ovarian carcinoma and HuH7 human hepatocellular carcinoma cells, in A431 cells there was no significant differences in yields/input virion for HSV-1 17+, HSV1716 or HSV1716EGFR. Thus, in 5/5 human cancer cell lines HSV1716ING4 replication was significantly more efficient compared to the parental HSV1716 or the HSV1716 variant HSV1716EGFR (expressing a similarly sized protein targeting moiety) and, compared to the wild-type HSV-1 17+, HSV1716ING4 replication was improved in ⅘ of these lines.

Further, when infected with either 10 pfu HSV-1 17+ or 10 pfu HSV1716, the yields/input virion were significantly enhanced 10-fold in 5 different clones of BHK cells engineered by transfection/antibiotic selection to constitutively express ING4 compared to BHK cells which derived antibiotic resistance from transfection with the empty pCDNA4 vector. Such BHK cells expressing ING4 constitutively may provide an improved substrate for propagation of HSV1716 and its variants, especially those with DNA inserts that restrict viral growth.

ING4 expression during HSV-1 17+/HSV1716 infection must act to improve the efficiency of virus replication within the cell resulting in a greater output of progeny virions per cell infected. Importantly, this enhancement to replication efficiency by ING4 did not compromise the HSV1716 phenotype as, in the animal tumour models, HSV1716ING4 was non-toxic and the virus failed to replicate in vitro in the HSV1716-resistant 3T6 cell line. ING4 may act directly on virus genes to improve their expression or interact directly with a viral protein to enhance its activity or, alternatively, it may act upon cellular genes/proteins to condition the cellular environment such that it is more amenable to virus replication. In vivo, this improvement to virus replication augments the oncolytic potency of HSV1716 resulting in more viruses for better tumour cell killing. Additionally, the other recognised activities of ING4, such as suppression of angiogenesis leading to a reduction in tumour vascularization, may also contribute to the enhanced oncolytic potency of HSV1716ING4.

REFERENCES

1. Gunduz, M., Nagatsuka, H., Demircan, K. et al., (2005) Gene 356; 109-117.
2. Garkavtsev, I., Kozin, S V., Chernova, O. et al., (2004) Nature 428; 328-332.
3. Doyon, Y., Cayrou, C., Ullah, M. et al., (2006) Molecular Cell 21; 51-64.
4. Ozer, A., Wu, L C., Bruick, R K, (2005) PNAS 102; 7481-7486.
5. Garkavtsev, I., Kazarov, A., Gudkov, A. and Riabowol, K. (1996) Nat. Genet. 14; 415-420.6. Russell, M., Berardi, P., Gong, W. and Riabowol, K. (2006) Exp. Cell Res. 312; 951-961.
7. Campos, E I., Chin, M Y., Kuo, W H. And Li, G. (2004) Cell Mol Life Sci 61; 597-613.
8. Shi, X. And Gozani, O. (2005) Cell Biochem. 96; 1127-1136.
9. Nagashima, M., Shiseki, M., Miura, K. et al. (2001) PNAS 98; 9671-9676.
10. Shiseki, M., Nagashima, M., Pedeux, R M. et al., (2003) Cancer Res. 63; 2373-2378.
11. Colla, S., Tagliaferri, S., Morandi, F. et al. (2007) Blood. DOI 10.1182/blood-2007-02-074617.
12. Shen, J-C., Unoki, M., Ythier, D. et al. (2007) Cancer Res. 67; 2552-2558.
13. Schellingerhout, D. et al. (1998) Human Gene Therapy 9; 1543-1549
14. Schellingerhout, D., Rainov, N G, Breakefield, X O. And Weissleder, R. (2000) Gene Therapy 7; 1648-1655

TABLE 1

Amounts of virus extracted from subcutaneous A431 SCC tumours following two intravenous injection of PBS or $1 \times 10^6$ pfu HSV1716 of HSV1716ING4 on days 1 and 3.

| treatment | Days post 1$^{st}$ administration | Total number of pfu from tumour |
|---|---|---|
| PBS control | 16 | 0 |
| PBS control | 16 | 0 |
| HSV1716 | 16 | $4.1 \times 10^3/2.1 \times 10^3$ |
| HSV1716 | 17 | 0 |
| HSV1716 | 17 | 0 |
| HSV1716ING4 | 16 | $3.6 \times 10^6/4.0 \times 10^6$ |
| HSV1716ING4 | 18 | $2.7 \times 10^6$ |
| HSV1716ING4 | 18 | $4.4 \times 10^6$ |

TABLE 2

Yields/input virion (pfu) from BHK cells infected with 100 pfu HSV-1 17+ HSV1716, HSV1716ING4 or HSV1716EGFR.

| replicate | HSV-1 17+ | HSV1716 | HSV1716ING4 | HSV1716EGFR |
|---|---|---|---|---|
| 1 | $9.2 \times 10^6$ | $3.9 \times 10^6$ | $4.4 \times 10^6$ | $5.3 \times 10^5$ |
| 2 | $6.9 \times 10^6$ | $4.4 \times 10^6$ | $4.0 \times 10^6$ | $6.7 \times 10^5$ |
| 3 | $7.3 \times 10^6$ | $3.4 \times 10^6$ | $3.6 \times 10^6$ | $7.4 \times 10^5$ |
| 4 | $6.6 \times 10^6$ | $4.8 \times 10^6$ | $3.7 \times 10^6$ | $4.5 \times 10^5$ |
| 5 | $6.1 \times 10^6$ | $4.4 \times 10^6$ | $4.7 \times 10^6$ | $3.3 \times 10^5$ |
| 6 | $1.1 \times 10^7$ | $6.3 \times 10^6$ | $4.7 \times 10^6$ | $2.4 \times 10^5$ |
| mean ± s.d. | $7.85 \times 10^6 \pm 1.88 \times 10^6$ | $4.54 \times 10^6 \pm 9.87 \times 10^5$ | $4.19 \times 10^6 \pm 4.83 \times 10^5$ | $4.93 \times 10^5 \pm 1.92 \times 10^5$ |

TABLE 3

Yields/input virion (pfu) from Vero cells infected with 1000 pfu HSV-1 17+ HSV1716, HSV1716ING4 or HSV1716EGFR.

| replicate | HSV-1 17+ | HSV1716 | HSV1716ING4 | HSV1716EGFR |
|---|---|---|---|---|
| 1 | $5.4 \times 10^5$ | $9.6 \times 10^5$ | $6.7 \times 10^5$ | $1.2 \times 10^5$ |
| 2 | $5.1 \times 10^5$ | $6.2 \times 10^5$ | $1.0 \times 10^6$ | $1.3 \times 10^5$ |
| 3 | $8.5 \times 10^5$ | $4.1 \times 10^5$ | $9.3 \times 10^5$ | $1.6 \times 10^5$ |
| 4 | $2.8 \times 10^5$ | $8.0 \times 10^5$ | $1.2 \times 10^6$ | $1.2 \times 10^5$ |
| 5 | $4.1 \times 10^5$ | $5.9 \times 10^5$ | $1.9 \times 10^6$ | $1.3 \times 10^5$ |
| 6 | $7.1 \times 10^5$ | $5.3 \times 10^5$ | $1.3 \times 10^6$ | $1.4 \times 10^5$ |
| mean ± s.d. | $5.50 \times 10^5 \pm 2.04 \times 10^5$ | $6.51 \times 10^5 \pm 1.97 \times 10^5$ | $1.20 \times 10^6 \pm 4.21 \times 10^5$ | $1.33 \times 10^5 \pm 1.51 \times 10^4$ |

TABLE 4

Yields/input virion (pfu) from human ovarian cancer Ovcar3 cells infected with 1000 pfu HSV-1 17+ HSV1716, HSV1716ING4 or HSV1716EGFR.

| replicate | HSV-1 17+ | HSV1716 | HSV1716ING4 | HSV1716EGFR |
|---|---|---|---|---|
| 1 | $7.3 \times 10^6$ | $3.7 \times 10^6$ | $1.6 \times 10^7$ | $8.5 \times 10^6$ |
| 2 | $9.5 \times 10^6$ | $3.8 \times 10^6$ | $1.4 \times 10^7$ | $5.7 \times 10^6$ |
| 3 | $5.9 \times 10^6$ | $3.4 \times 10^6$ | $1.9 \times 10^7$ | $7.4 \times 10^6$ |
| 4 | $7.8 \times 10^6$ | $3.3 \times 10^6$ | $1.4 \times 10^7$ | $5.4 \times 10^6$ |
| mean ± s.d. | $7.63 \times 10^6 \pm 1.49 \times 10^6$ | $3.55 \times 10^6 \pm 2.38 \times 10^5$ | $1.58 \times 10^7 \pm 2.36 \times 10^6$ | $6.76 \times 10^6 \pm 1.45 \times 10^6$ |

TABLE 5

Yields/input virion (pfu) from A431 human SCC cells infected with 1000 pfu HSV-1 17+ HSV1716, HSV1716ING4 or HSV1716EGFR.

| replicate | HSV-1 17+ | HSV1716 | HSV1716ING4 | HSV1716EGFR |
|---|---|---|---|---|
| 1 | 63000 | 946 | 87000 | 18400 |
| 2 | 93000 | 1389 | 39000 | 13000 |
| 3 | 57000 | 1088 | 261000 | 10000 |
| 4 | 95000 | 1327 | 113000 | 11800 |
| mean ± s.d. | 77000 ± 19799 | 1188 ± 207 | 125000 ± 95708 | 13300 ± 3617 |

TABLE 6

Yields/input virion (pfu) from the human breast adenocarcinoma MDA-MB-468 cell line infected with 1000 pfu HSV-1 17+ HSV1716, HSV1716ING4 or HSV1716EGFR.

| replicate | HSV-1 17+ | HSV1716 | HSV1716ING4 | HSV1716EGFR |
|---|---|---|---|---|
| 1 | 61000 | 74100 | 910000 | 68000 |
| 2 | 69000 | 79000 | 590000 | 66000 |
| 3 | 57000 | 71000 | 780000 | 65000 |
| 4 | 32000 | 66000 | 680000 | 86000 |
| mean ± s.d. | 54750 ± 15966 | 72525 ± 5456 | 740000 ± 137356 | 71250 ± 9912 |

TABLE 7

Yields/input virion (pfu) from the human ovarian cancer cell line CP70 infected with 1000 pfu HSV-1 17+ HSV1716, HSV1716ING4 or HSV1716EGFR.

| replicate | HSV-1 17+ | HSV1716 | HSV1716ING4 | HSV1716EGFR |
|---|---|---|---|---|
| 1 | 840 | 800 | 1450 | 536 |
| 2 | 1350 | 750 | 1670 | 353 |
| 3 | 2700 | 480 | 1670 | 360 |
| 4 | 1091 | 566 | 1340 | 408 |
| 5 | 1500 | 258 | 1920 | 496 |
| mean ± s.d. | 1496 ± 718 | 571 ± 218 | 1610 ± 224 | 430 ± 82 |

TABLE 8

Yields/input virion (pfu) for the human hepatocellular carcinoma cell line HuH7 infected with 1000 pfu HSV-1 17+ HSV1716, HSV1716ING4 or HSV1716EGFR.

| replicate | HSV-1 17+ | HSV1716 | HSV1716ING4 | HSV1716EGFR |
|---|---|---|---|---|
| 1 | 9647 | 14769 | 62667 | 1760 |
| 2 | 12941 | 14215 | 95556 | 2187 |
| 3 | 13129 | 17046 | 86667 | 3413 |
| 4 | 9976 | 17230 | 71556 | 2933 |
| 5 | 8517 | 17969 | 69333 | 3893 |
| mean ± s.d. | 10842 ± 2075 | 16246 ± 1650 | 77156 ± 13523 | 2837 ± 871 |

TABLE 9

Yields/input virion (pfu) from 5 different clones of either BHK/ING4 or BHK/pCDNA4 infected with 100 pfu HSV17+

| Clone | BHK/ING4 | BHK/pCDNA4 |
|---|---|---|
| 1 | $4.45 \times 10^7$ | $5.3 \times 10^6$ |
| 2 | $8.96 \times 10^7$ | $2.6 \times 10^6$ |
| 3 | $8.76 \times 10^7$ | $3.8 \times 10^6$ |
| 4 | $8.68 \times 10^7$ | $2.6 \times 10^6$ |
| 5 | $1.13 \times 10^8$ | $2.0 \times 10^6$ |
| Mean ± s.d. | $8.43 \times 10^7 \pm 2.48 \times 10^7$ | $3.26 \times 10^6 \pm 1.32 \times 10^6$ |

TABLE 10

Yields/input virion (pfu) from 5 different clones of either BHK/ING4 or BHK/pCDNA4 infected with 100 pfu HSV1716

| Clone | BHK/ING4 | BHK/pCDNA4 |
|---|---|---|
| 1 | $2.6 \times 10^7$ | $1.8 \times 10^6$ |
| 2 | $2.1 \times 10^7$ | $1.0 \times 10^6$ |
| 3 | $9.2 \times 10^6$ | $1.3 \times 10^6$ |
| 4 | $7.24 \times 10^7$ | $2.5 \times 10^6$ |
| 5 | $7.36 \times 10^7$ | $2.2 \times 10^6$ |
| Mean ± s.d. | $8.724 \times 10^7 \pm 1.009 \times 10^8$ | $1.766 \times 10^6 \pm 6.19 \times 10^5$ |

TABLE 11

Total yields from different cell types following infection with 1 pfu HSV1716, HSV1716EGFR or HSV1716/ING4.

| virus | 3T6 | MDA | UVW | A431 | CP70 | Vero | Ovcar3 | BHK |
|---|---|---|---|---|---|---|---|---|
| 1716 | 0 | 0 | 0 | $4 \times 10^4$ | $2 \times 10^4$ | $1 \times 10^5$ | $1 \times 10^6$ | $1 \times 10^7$ |
| EGFR | 0 | 0 | 0 | $5 \times 10^4$ | $2 \times 10^4$ | $2 \times 10^5$ | $1 \times 10^6$ | $4 \times 10^6$ |
| ING4 | 0 | $1 \times 10^3$ | $1 \times 10^3$ | $6 \times 10^4$ | $4 \times 10^4$ | $4 \times 10^5$ | $3 \times 10^7$ | $2 \times 10^7$ |

TABLE 12

Total yields from different cell types following infection with 10 pfu HSV1716, HSV1716EGFR or HSV1716/ING4.

| virus | 3T6 | MDA | UVW | A431 | CP70 | Vero | Ovcar3 | BHK |
|---|---|---|---|---|---|---|---|---|
| 1716 | 0 | 0 | $1 \times 10^4$ | $4 \times 10^5$ | $6 \times 10^4$ | $6 \times 10^5$ | $1 \times 10^6$ | $1 \times 10^7$ |
| EGFR | 0 | 0 | $6 \times 10^3$ | $8 \times 10^5$ | $4 \times 10^4$ | $4 \times 10^5$ | $6 \times 10^7$ | $4 \times 10^6$ |
| ING4 | 0 | $1 \times 10^4$ | $2 \times 10^4$ | $7.2 \times 10^5$ | $1 \times 10^5$ | $2 \times 10^7$ | $2 \times 10^8$ | $4 \times 10^7$ |

TABLE 13

Total yields from different cell types following infection with 100 pfu HSV1716, HSV1716EGFR or HSV1716/ING4.

| virus | 3T6 | MDA | UVW | A431 | CP70 | Vero | Ovcar3 | BHK |
|---|---|---|---|---|---|---|---|---|
| 1716 | 0 | $2 \times 10^3$ | $7.2 \times 10^4$ | $6 \times 10^5$ | $3 \times 10^5$ | $6 \times 10^6$ | $5 \times 10^7$ | $1 \times 10^8$ |
| EGFR | 0 | $3 \times 10^4$ | $6 \times 10^4$ | $6 \times 10^6$ | $4 \times 10^5$ | $8 \times 10^6$ | $8 \times 10^7$ | $8 \times 10^7$ |
| ING4 | 0 | $4 \times 10^4$ | $4 \times 10^5$ | $5 \times 10^6$ | $8 \times 10^5$ | $3 \times 10^7$ | $4 \times 10^8$ | $3 \times 10^8$ |

TABLE 14

Ratios of yields (HSV1716ING4:HSV1716) in each of the different cell types following infections at 1, 10 or 100 pfu.

| | Cell type | | | | | | |
|---|---|---|---|---|---|---|---|
| input | BHK | Vero | UVW | MDA | CP70 | A431 | Ovcar3 |
| 1 pfu | 2:1 | 4:1 | n.d.* | n.d. | 2:1 | 3:2 | 30:1 |
| 10 pfu | 4:1 | 30:1 | 2:1 | n.d | 2:1 | 2:1 | 200:1 |
| 100 pfu | 3:1 | 5:1 | 6:1 | 20:1 | 3:1 | 10:1 | 10:1 |

*n.d. = not determinable as yield for HSV1716 was 0.

TABLE 15

Total virus yields from different cell types following duplicate infections with 5 pfu HSV1716, HSV1716EGFR or HSV1716/ING4.

| | Cell type | | | | | | |
|---|---|---|---|---|---|---|---|
| virus | BHK | Ovcar 3 | Vero | A431 | CP70 | MDA | UVW |
| ING4 | $2 \times 10^8$ | $2 \times 10^8$ | $5 \times 10^6$ | $1.25 \times 10^7$ | $2.5 \times 10^5$ | $2 \times 10^5$ | $2.5 \times 10^5$ |
| ING4 | $1.5 \times 10^8$ | $5 \times 10^8$ | $1.5 \times 10^7$ | $1 \times 10^7$ | $1.8 \times 10^5$ | $2 \times 10^5$ | $2.5 \times 10^5$ |
| EGFR | $7.5 \times 10^7$ | $1.5 \times 10^7$ | $1.5 \times 10^6$ | $2.3 \times 10^6$ | $1.25 \times 10^5$ | $1 \times 10^5$ | $5 \times 10^3$ |
| EGFR | $1.3 \times 10^8$ | $1.8 \times 10^7$ | $1.5 \times 10^6$ | $2 \times 10^6$ | $1.5 \times 10^5$ | $1.3 \times 10^5$ | $7.5 \times 10^3$ |
| 1716 | $1 \times 10^8$ | $2 \times 10^6$ | $1.8 \times 10^5$ | $1.3 \times 10^5$ | $1.5 \times 10^4$ | $1.2 \times 10^4$ | $1 \times 10^3$ |
| 1716 | $3.5 \times 10^8$ | $2.5 \times 10^6$ | $1.5 \times 10^5$ | $1.5 \times 10^5$ | $1.2 \times 10^4$ | $1.7 \times 10^4$ | $2 \times 10^3$ |

TABLE 16

Total virus yields from different cell types following duplicate infections with 20 pfu HSV1716, HSV1716EGFR or HSV1716/ING4.

| | Cell type | | | | | | |
|---|---|---|---|---|---|---|---|
| virus | BHK | Ovcar 3 | Vero | A431 | CP70 | MDA | UVW |
| ING4 | $6 \times 10^8$ | $1 \times 10^9$ | $1 \times 10^7$ | $1.5 \times 10^7$ | $1.5 \times 10^5$ | $1 \times 10^6$ | $5 \times 10^4$ |
| ING4 | $2 \times 10^8$ | $5 \times 10^8$ | $2.5 \times 10^6$ | $1.75 \times 10^7$ | $1 \times 10^5$ | $2.5 \times 10^5$ | $1 \times 10^4$ |
| EGFR | $1 \times 10^8$ | $1.5 \times 10^7$ | $1 \times 10^6$ | $1 \times 10^6$ | $1 \times 10^4$ | $1 \times 10^5$ | 0 |
| EGFR | $3 \times 10^8$ | $1.75 \times 10^7$ | $1.25 \times 10^6$ | $1 \times 10^6$ | $3 \times 10^4$ | $1.25 \times 10^5$ | 0 |
| 1716 | $1.75 \times 10^8$ | $1.25 \times 10^7$ | $1.5 \times 10^5$ | $1 \times 10^6$ | $7.5 \times 10^4$ | $2 \times 10^4$ | $2 \times 10^3$ |
| 1716 | $1.5 \times 10^8$ | $2.5 \times 10^7$ | $1.5 \times 10^5$ | $1.25 \times 10^6$ | $1 \times 10^5$ | $2 \times 10^4$ | $5 \times 10^3$ |

TABLE 17

Ratios of yields of HSV1716ING4:HSV1716 in each of the different cell types following infections at 5 or 20 pfu.

| | Cell type | | | | | | |
|---|---|---|---|---|---|---|---|
| input | BHK | Ovcar3 | Vero | A431 | CP70 | MDA | UVW |
| 5 pfu | 2:1 | 100:1 | 30:1 | 100:1 | 10:1 | 20:1 | 25:1 |
| 5 pfu | 4:1 | 200:1 | 100:1 | 66:1 | 10:1 | 10:1 | 10:1 |
| 20 pfu | 4:1 | 40:1 | 66:1 | 15:1 | 1:1 | 10:1 | 10:1 |
| 20 pfu | 1:1 | 50:1 | 20:1 | 50:1 | 2:1 | 50:1 | 5:1 |

TABLE 18

Total amounts of virus produced/flask, % yields (output/input) and the ratio of yield/cell type compared to the HSV1716 % yield/cell type for infection of T175 flasks with HSV-1 17+, HSV1716, HSV1716EGFR or HSV1716ING4.

| Virus | Input (pfu) | Yield (pfu) | % yield* | Ratio** | Input (pfu) | Yield (pfu) | % yield* | Ratio** |
|---|---|---|---|---|---|---|---|---|
| | BHK | | | | UVW | | | |
| 17+ | 1000 | $5.9 \times 10^{10}$ | $5 \times 10^7$ | 1:1 | 100,000 | $5.9 \times 10^8$ | 5900 | 8:1 |
| 1716 | 690 | $3.5 \times 10^{10}$ | $5 \times 10^7$ | | 69,000 | $4.8 \times 10^7$ | 700 | |
| EGFR | 1680 | $3.6 \times 10^{10}$ | $2 \times 10^7$ | 1:1 | 168,000 | $2.1 \times 10^5$ | 2 | 1:350 |
| ING4 | 175 | $4.0 \times 10^{10}$ | $2 \times 10^8$ | 4:1 | 17,500 | $1.4 \times 10^8$ | 7714 | 10:1 |
| | A431 | | | | Ovcar3 | | | |
| 17+ | 100,000 | $7.2 \times 10^8$ | 7200 | 2:1 | 100,000 | $4.2 \times 10^8$ | 4200 | 10:1 |
| 1716 | 69,000 | $3.4 \times 10^8$ | 4900 | | 69,000 | $2.5 \times 10^7$ | 360 | |
| EGFR | 168,000 | $6.6 \times 10^8$ | 3900 | 1:1 | 168,000 | $3.9 \times 10^8$ | 2300 | 7:1 |
| ING4 | 17,500 | $3.7 \times 10^8$ | 21,000 | 5:1 | 17,500 | $1.5 \times 10^8$ | 8571 | 25:1 |
| | MDA | | | | CP70 | | | |
| 17+ | 100,000 | $1 \times 10^6$ | 10 | 10:1 | 100,000 | $3.8 \times 10^8$ | 3800 | 36:1 |
| 1716 | 69,000 | $4.6 \times 10^4$ | 1 | | 69,000 | $7.6 \times 10^6$ | 110 | |
| EGFR | 168,000 | $1.8 \times 10^5$ | 1 | 1 | 168,000 | $9.2 \times 10^6$ | 55 | 1:2 |
| ING4 | 17,500 | $7.2 \times 10^4$ | 4 | 4:1 | 17,500 | $7.3 \times 10^6$ | 417 | 4:1 |

| | | Vero | | |
|---|---|---|---|---|
| Virus | Input (pfu) | Yield (pfu) | % yield* | Ratio** |
| 17+ | 100,000 | $1.1 \times 10^8$ | 1100 | 11:1 |
| 1716 | 69,000 | $6.9 \times 10^6$ | 100 | |
| EGFR | 168,000 | $3 \times 10^7$ | 177 | 1.7:1 |
| ING4 | 17,500 | $2.9 \times 10^7$ | 1657 | 16:1 |

*amount of output virus/amount input virus
**ratio of % yield virus relative to % yield HSV1716

The invention claimed is:

1. A method of replicating herpes simplex virus (HSV) in vitro, the method comprising replicating HSV in vitro in cells having ING4 polypeptide in excess of the amount normally present from endogenous expression of said cells wherein the ING4 polypeptide has at least 95% sequence identity to SEQ ID NO: 3.

2. The method of claim 1, wherein the cell(s) express ING4 polypeptide from a vector transfected into the cell(s).

3. The method of claim 1, wherein the cell(s) express ING4 polypeptide from a heterologous construct comprising a nucleic acid sequence encoding an ING4 polypeptide.

4. The method of claim 1, wherein the cell(s) express ING4 polypeptide from a heterologous construct comprising a nucleic acid sequence encoding an ING4 polypeptide operably linked to a regulatory nucleotide sequence.

5. The method of claim 3, wherein expression of said nucleic acid sequence encoding ING4 polypeptide is constitutive.

6. The method of claim 1, wherein the cell(s) overexpress endogenous ING4 polypeptide.

7. The method of claim 1, wherein the HSV is selected from the group consisting of an HSV-1, HSV-1 strain 17, HSV1716, HSV1716 ING4, HSV-1 strain F, and HSV-1 strain F mutant G207.

8. A method for the in vitro replication of herpes simplex virus (HSV), the method comprising infecting a cell or cells with HSV, culturing the cell(s) in vitro, and harvesting viral progeny from the cell(s), wherein the cells have ING4 polypeptide in excess of the amount normally present from endogenous expression of said cells, and wherein the ING4 polypeptide has at least 95% sequence identity to SEQ ID NO:3.

9. The method of claim 8, wherein the cell(s) express ING4 polypeptide from a vector transfected into the cell(s).

10. The method of claim 8, wherein the cell(s) express ING4 polypeptide from a heterologous construct comprising a nucleic acid sequence encoding an ING4 polypeptide.

11. The method of claim 8, wherein the cell(s) express ING4 polypeptide from a heterologous construct comprising a nucleic acid sequence encoding an ING4 polypeptide operably linked to a regulatory nucleotide sequence.

12. The method of claim 10, wherein expression of said nucleic acid sequence encoding ING4 polypeptide is constitutive.

13. The method of claim 8, wherein the cell(s) overexpress endogenous ING4 polypeptide.

14. The method of claim 8, wherein the HSV is selected from the group consisting of an HSV-1, HSV-1 strain 17, HSV1716, HSV1716ING4, HSV-1 strain F, and HSV-1 strain F mutant G207.

15. A cell, in vitro, infected with a herpes simplex virus, which cell has ING4 polypeptide in excess of the amount normally present from endogenous expression of said cells, wherein the ING4 polypeptide has at least 95% sequence identity to SEQ ID NO:3.

16. A cell according to claim 15, wherein the cell expresses ING4 polypeptide from a heterologous construct comprising a nucleic acid sequence encoding an ING4 polypeptide.

17. A cell according to claim 15, wherein the cell overexpresses endogenous ING4 polypeptide.

* * * * *